(12) United States Patent
Gray et al.

(10) Patent No.: US 10,980,765 B2
(45) Date of Patent: Apr. 20, 2021

(54) ISOTHIOCYANATOSTILBENES AS A NOVEL METHOD AND PRODUCT FOR TREATING CANCER

(71) Applicant: BOARD OF SUPERVISORS OF LOUISIANA STATE UNIVERSITY AND AGRICULTURAL AND MECHANICAL COLLEGE, Baton Rouge, LA (US)

(72) Inventors: Alana Lea Gray, Shreveport, LA (US); James Cardelli, Shreveport, LA (US); David Thomas Coleman, Shreveport, LA (US); Khalid El-Sayed, West Monroe, LA (US); Mohamed M. Mohyeldin, Monroe, LA (US)

(73) Assignees: BOARD OF SUPERVISORS OF LOUISIANA STATE UNIVERSITY, Baton Rouge, LA (US); BOARD OF SUPERVISORS FOR THE UNIVERSITY OF LOUISIA, Monroe, LA (US)

( * ) Notice: Subject to any disclaimer, the term of this patent is extended or adjusted under 35 U.S.C. 154(b) by 0 days.

(21) Appl. No.: 15/752,360

(22) PCT Filed: Aug. 15, 2016

(86) PCT No.: PCT/US2016/046989
§ 371 (c)(1),
(2) Date: Feb. 13, 2018

(87) PCT Pub. No.: WO2017/031036
PCT Pub. Date: Feb. 23, 2017

(65) Prior Publication Data
US 2019/0000791 A1 Jan. 3, 2019

Related U.S. Application Data

(60) Provisional application No. 62/205,106, filed on Aug. 14, 2015.

(51) Int. Cl.
*A61K 31/26* (2006.01)
*A61K 45/06* (2006.01)
*A61K 31/185* (2006.01)

(52) U.S. Cl.
CPC .......... *A61K 31/26* (2013.01); *A61K 31/185* (2013.01); *A61K 45/06* (2013.01)

(58) Field of Classification Search
CPC ..................................... A61K 31/26
See application file for complete search history.

(56) References Cited

U.S. PATENT DOCUMENTS

| 2008/0171793 A1 | 7/2008 | Verkman et al. |
| 2011/0237540 A1* | 9/2011 | Crawford ............. A61K 31/337 514/58 |
| 2013/0184342 A1* | 7/2013 | Mills .................. G01N 33/5008 514/516 |

OTHER PUBLICATIONS

Mills et al. CAS: 159:253856, 2013.*
Katayama et al. Cancer Research, 2013, 73(10):3087-96.*
Girotra et al., "Supercritical Fluid Technology: A Promising Approach in Pharmaceutical Research", Pharmaceutical Development and Technology, 2013, vol. 18, pp. 22-38.
Ishida et al., "DIDS, A Chemical Compound that Inhibits RAD51-Mediated Homologous Pairing and Strand Exchange", Nucleic Acid Research, Mar. 30, 2009, vol. 37, pp. 3367-3376.
Nikhil et al., "Pterostilbene-Isothiocyanate Conjugate Suppresses Growth of Prostate Cancer Cells Irrespective of Androgen Receptor Status", PLOS ONE, Apr. 3, 2014, vol. 9, e93335.
International Search Report Corresponding to PCT/US2016/046989 dated Oct. 28, 2016.
Written Opinion Corresponding to PCT/US2016/046989 dated Oct. 28, 2016.

* cited by examiner

*Primary Examiner* — Rei Tsang Shiao
(74) *Attorney, Agent, or Firm* — Davis & Bujold, P.L.L.C.; Charles G. Holoubek

(57) ABSTRACT

Products and methods for treating cancer in a human patient comprising administering to the patient therapeutically effective amount of a first pharmaceutically active agent, wherein the first pharmaceutically active agent is one of an isothiocyanatostilbene and a pharmacologically acceptable salt, solvate, ester, amide, clathrate, stereoisomer, enantiomer, prodrug or analog thereof, or a combination thereof.

19 Claims, 15 Drawing Sheets

Fig. 1A
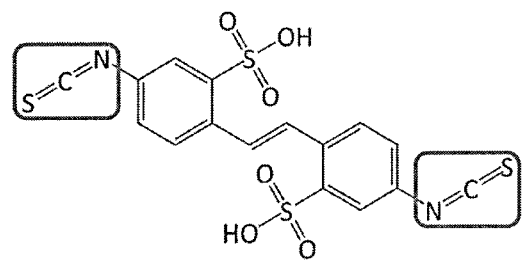
4,4'-Diisothiocyanatostilbene-2,2'-disulfonic acid (DIDS)
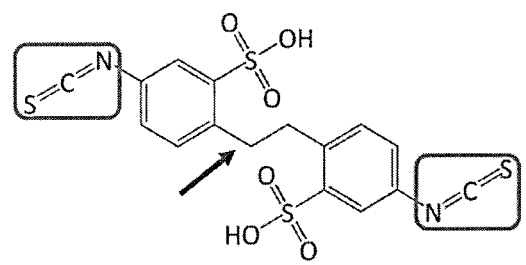
4,4'-Diisothiocyanatodihydrostilbene-2,2'-disulfonic acid (H2DIDS)
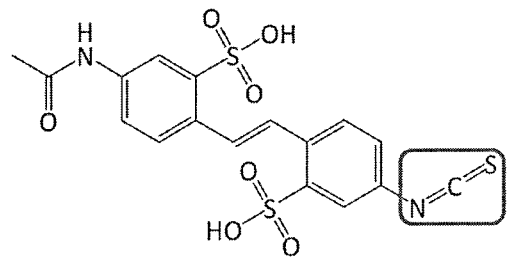
4,4'-Acetamido-4'-isothiocyanatostilbene-2,2'disulfonic acid (SITS)
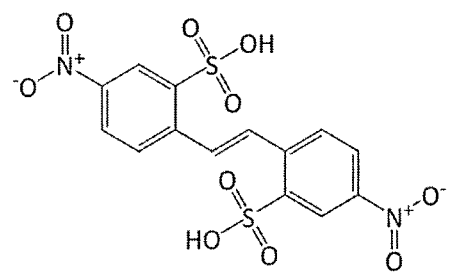
4,4'-Dinitrostilbene-2,2'-disulfonic acid (DNDS)

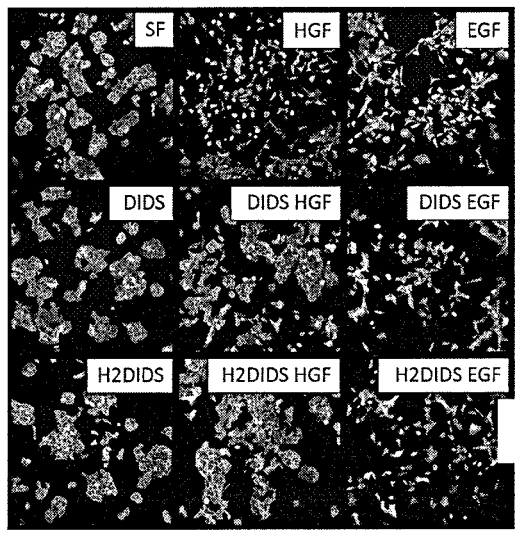
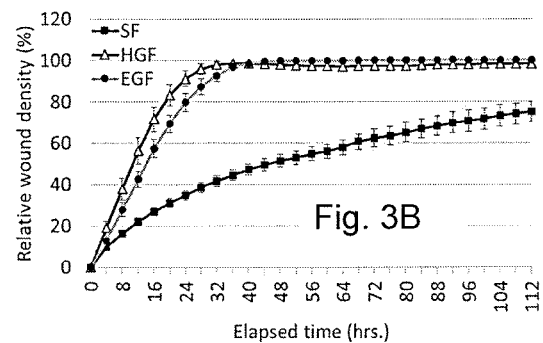
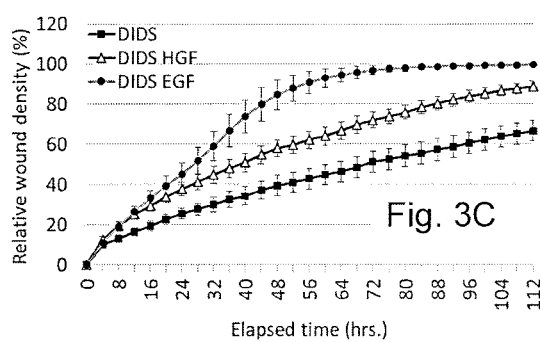
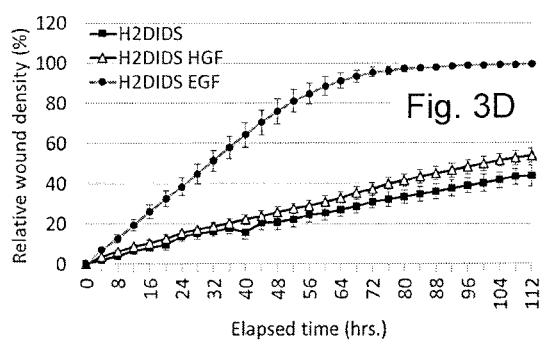
Fig. 3A
Fig. 3B
Fig. 3C
Fig. 3D

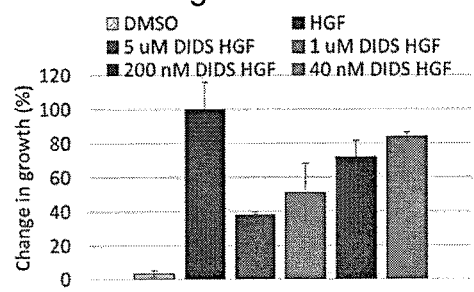 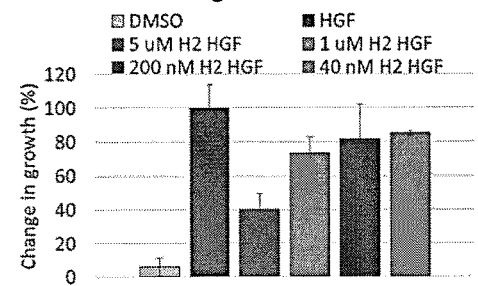
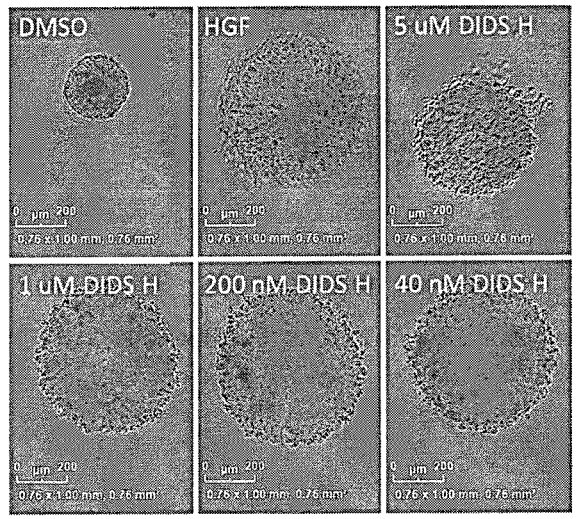 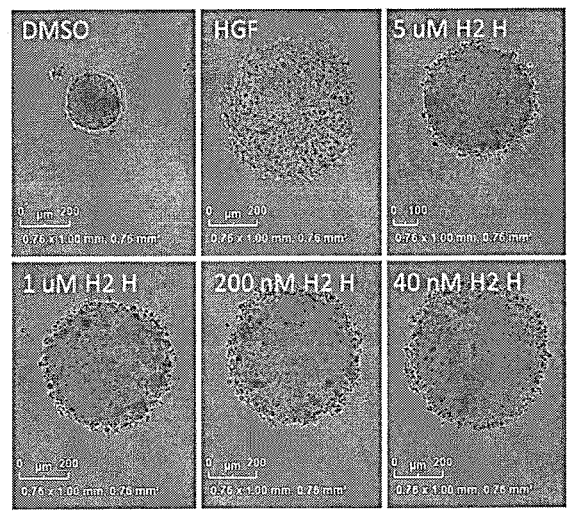

ISOTHIOCYANATOSTILBENES AS A NOVEL METHOD AND PRODUCT FOR TREATING CANCER

CROSS REFERENCE TO RELATED APPLICATIONS/PRIORITY

The present invention claims priority to U.S. Provisional Patent Application No. 62/205,106 filed Aug. 14, 2015, which is incorporated by reference into the present disclosure as if fully restated herein. To the extent that there is any conflict between the incorporated material and the present disclosure, the present disclosure will control.

STATEMENT REGARDING FEDERALLY SPONSORED RESEARCH OR DEVELOPMENT

The subject matter disclosed herein was partly supported by the National Cancer Institute of the National Institutes of Health under Award Number R15CA167475 (KE).

FIELD OF THE INVENTION

The present invention relates to a method and product for treating cancer and particularly to administering isothiocyanatostilbenes to inhibit the hepatocyte growth factor receptor.

BACKGROUND

The hepatocyte growth factor receptor (HGFR or c-Met) is a driver of multiple cancer subtypes. The c-Met receptor tyrosine kinase has been demonstrated to be sufficient for oncogenic transformation, is a major regulator of invasive growth, and is a key contributor to tumor progression. C-Met is an established therapeutic target for multiple types of cancers. Studies have shown that targeting the c-Met pathway can prevent and, in some cases, even reverse advanced stages of tumor progression as evidenced by a reduction in the number and size of metastatic lesions. While several tyrosine kinase inhibitors (TKIs) have been identified as moderately effective anti-cancer therapies, they are often prove prohibitively toxic to the patient and it is also common for patients to develop an acquired resistance to these drugs. Because of this, there is a continued need for the development of an expanded repertoire of tyrosine kinase inhibitors.

A recent search of ClinicalTrials.gov revealed over 50 ongoing studies examining the role of c-Met in cancer. However, the inventors are aware of only two currently FDA-approved c-Met inhibitors: crizotinib (Xalkori; Pfizer) and cabozantinib (Cometriq; Exelixis). Both of these compounds are non-specific c-Met inhibitors, such that crizotinib also targets ROS proto-oncogene 1, receptor tyrosine kinase (ROS1) and anaplastic lymphoma kinase (ALK) while cabozantinib inhibits vascular endothelial growth factor receptor 2 (VEGFR2), in addition to c-Met.

The c-Met pathway has been shown to be involved in normal homeostatic functions, but the dysregulation of this c-Met signaling can result in various pathological outcomes, including cancer. Activation of the c-Met receptor classically occurs following binding of its only known ligand, hepatocyte growth factor (HGF) prior to c-Met dimerization. This dimerization triggers multiple autophosphorylation events of the cytoplasmic tail of c-Met that are required for propagation of downstream signaling leading to increased cell proliferation, motility, and tumor cell invasion and metastasis. Multiple approaches targeting aberrant signaling through the c-Met pathway have been employed including anti-HGF and anti-c-Met antibodies, HGF and c-Met competitive antagonists, and inhibitors of signaling molecules downstream of c-Met activation.

SUMMARY OF THE INVENTION

Wherefore, it is an object of the present invention to overcome the above mentioned shortcomings and drawbacks associated with the prior art.

The research disclosed herein demonstrates a particular class of compounds known as isothiocyanatostilbenes that the inventors discovered act as c-Met inhibitors in multiple cancer cell lines. Specifically, the inventors found that 4,4'-Diisothiocyanatostilbene-2,2'-disulfonic acid (DIDS) and 4,4'-Diisothiocyanatodihydrostilbene-2,2'-disulfonic acid (H2DIDS) had c-Met inhibitory effective doses in the low micromolar range while 4-acetamido-4'-isothiocyanatostilbene-2,2'-disulfonic acid (SITS) and 4,4'-dinitrostilbene-2,2'-disulfonic acid (DNDS) exhibited $IC_{50}$s 100 to 1000 fold higher. These compounds displayed much greater selectivity for inhibiting c-Met activation compared to similar receptor tyrosine kinases. In addition, DIDS and H2DIDS reduced hepatocyte growth factor (HGF)-induced, but not epidermal growth factor (EGF)-induced, cell scattering, wound healing, and 3-dimensional (3D) proliferation of tumor cell spheroids. In-cell and cell-free assays evidence that DIDS and H2DIDS inhibits and reverses c-Met phosphorylation. Additional data demonstrated that DIDS is tolerable in vivo and slows growth of breast cancer tumors. These data provide support for using DIDS, H2DIDS, and derivatives as c-Met therapeutics, especially with cancers where c-MET is deregulated or c-Met inhibition would otherwise be therapeutic, including cancers of kidney, liver, stomach, breast, brain, lung, ovary, colon, gastric, thyroid, pancreas, head and neck, prostate, liver, and essentially all solid tumors of different organs.

The present invention also relates to a method for treating cancer in a human patient comprising administering to the patient therapeutically effective amount of isothiocyanatostilbenes.

The invention relates to products and methods for treating cancer in a human patient including administering to the patient therapeutically effective amount of a first pharmaceutically active agent, wherein the first pharmaceutically active agent is one of an isothiocyanatostilbene and a pharmacologically acceptable salt, solvate, ester, amide, clathrate, stereoisomer, enantiomer, prodrug or analog thereof, or a combination thereof.

In further embodiments the cancer is selected from a group consisting of cancers of the kidney, liver, stomach, breast, brain, lung, ovary, colon, gastric, thyroid, pancreas, head and neck, prostate, and liver. In further embodiments the cancer is a solid tumor. In further embodiments the isothiocyanatostilbene is selected from a group consisting of 4,4'-Diisothiocyanatostilbene-2,2'-disulfonic acid (DIDS), 4,4'-Diisothiocyanatodihydrostilbene-2,2'-disulfonic acid (H2DIDS), 4-acetamido-4'-isothiocyanatostilbene-2,2'-disulfonic acid (SITS), and 4,4'-dinitrostilbene-2,2'-disulfonic acid (DNDS), and a pharmacologically acceptable salt, solvate, ester, amide, clathrate, stereoisomer, enantiomer, prodrug or analog thereof, or a combination thereof. Further embodiments comprise the step of administering to the patient a therapeutically effective amount of a first further pharmaceutically active agent. In further embodiments the first further pharmaceutically active agent is a c-Met inhibitor. In further embodiments the c-Met inhibitor of one of Crizotinib (PF-02341066), Cabozantinib (XL184, BMS-907351), Foretinib (GSK1363089), PHA-665752, SU11274, SGX-523, BMS-777607, Tivantinib (ARQ 197), JNJ-38877605, PF-04217903, MGCD-265, Capmatinib (INCB28060), BMS-754807, BMS-794833, AMG-208, MK-2461, Golvatinib (E7050), AMG-458, Tepotinib (EMD 1214063), NVP-BVU972, and NPS-1034, and a pharmacologically acceptable salt, solvate, ester, amide, clathrate, stereoisomer, enantiomer, prodrug or analog thereof, or a combination thereof. In further embodiments the first further pharmaceutically active agent is one or more of (1) additional isothiocyanatostilbene distinct from the first pharmaceutically active agent, (2) a receptor tyrosine kinase inhibitor (RTKi), (3) an agent that targets non-receptor tyrosine kinases, (4) an anti-cell proliferative chemotherapeutic agent, or of a pharmacologically acceptable salt, solvate, ester, amide, clathrate, stereoisomer, enantiomer, prodrug or analog thereof. Further embodiments comprise the step of administering to the patient a therapeutically effective amount of a second further pharmaceutically active agent, where the second pharmaceutically active agent is a further one of an isothiocyanatostilbene and a pharmacologically acceptable salt, solvate, ester, amide, clathrate, stereoisomer, enantiomer, prodrug or analog thereof, or a combination thereof, and the first pharmaceutically active agent is distinct from the second pharmaceutically active agent. In further embodiments the first pharmaceutically active agent is a isothiocyanatostilbene that has been chemically modified to increase one of bioavailability. In further embodiments the pharmaceutically active agent is in a cyclodextrin conjugation. In further embodiments the cyclodextrin conjugation is one of an α-cyclodextrin (α-CD) conjugation, a β-cyclodextrin (β-CD) conjugation, and a γ-cyclodextrin (γ-CD) conjugation. In further embodiments the pharmaceutically active agent is formed as nanoparticles. In further embodiments the nanoparticles are formed using solution-enhanced dispersion by supercritical carbon dioxide.

The invention further relates to methods and therapeutic products including a first pharmaceutically active agent being one of an isothiocyanatostilbene, and a pharmacologically acceptable salt, solvate, ester, amide, clathrate, stereoisomer, enantiomer, prodrug or analog thereof, or a combination thereof; and a further pharmaceutically active agent. In further embodiments the further pharmaceutically active agent is one or more additional isothiocyanatostilbenes, or a pharmacologically acceptable salt, solvate, ester, amide, clathrate, stereoisomer, enantiomer, prodrug or analog thereof, distinct from the first pharmaceutically active agent. In further embodiments the further pharmaceutically active agent is one or more receptor tyrosine kinase inhibitors; a receptor tyrosine kinase inhibited is one of c-Met, RON, ROS, EGFR1, EGFR2, EGFR3, EGFR4, EGRFvIII, c-Kit, c-FMS, FLT3, PDGFR, IGFR, VEGFR, VEGR2, TIE-1, TIE-2, PTK-7, FGFR1-3, TRKA-C, RORs, BCR-ABL, EPHA1-5, EPHB1-4, and RET: and the receptor tyrosine kinase inhibitor is one of Alectinib, Axitinib, Crizotinib, Cabozantinib, Centinib, Erlotinib, Gefitinib, Lapatinib, Lenvatinib, Osimertinib, Pazopanib, Ponatinib, Regorafenib, Sorafenib, Sunitinib, Tofacitinib, Vandetanib, and Vismodegib. In further embodiments the further pharmaceutically active agent is one or more agents that target non-receptor tyrosine kinases; the non-receptor tyrosine kinase is one of ABL1-2, ACK1, BLK, Bmx, bRAF, BRK, BTK, CSK, FAK, FES, FRK, FYNA, HCK, ITK, Jakl-2, LCK, Lok1, LRRK2, LYNA-B, MNK1, MEK, mTOR, PI3K, PYK2, Src, Syk, Zap-70, and CDK4: and the agent that targets the non-receptor tyrosine kinase is one of Bosultinib, Cobimetinib, Dabrafenib, Dasatinib, Everolimus, Ibrutinib, Idelalisib, Imatinib, nilotinib, Palbociclib, Ponatinib, Rogorafenib, Ruxolitinib, Temsirolimus, and Trametinib. In further embodiments the further pharmaceutically active agent is one or more anti-cell proliferative chemotherapeutic agent and the anti-cell proliferative chemotherapeutic agent is one of an anti-cancer and anti-tumor drug; an alkylating agent, anti-metabolite, plant extract, plant alkaloid, nitrosourea, hormone, nucleoside analog, and nucleotide analog; and 5-fluorouracil, cyclophosphamide, azathioprine, cyclosporin A, prednisolone, melphalan, chlorambucil, mechlorethamine, busulphan, methotrexate, 6-mercaptopurine, thioguanine, cytosine arabinoside, AZT, 5-azacytidine (5-AZC), bleomycin, actinomycin D, mithramycin, mitomycin C, carmustine, lomustine, semustine, streptozotocin, hydroxyurea, cisplatin, carboplatin, oxiplatin, mitotane, procarbazine, dacarbazine, taxol (paclitaxel), Nab-paclitaxel, vinblastine, vincristine, doxorubicin, dibromomannitol, irinotecan, topotecan, etoposide, teniposide, or pemetrexed.

The invention further relates to methods and therapeutic products including a first pharmaceutically active agent being one of an isothiocyanatostilbene, and a pharmacologically acceptable salt, solvate, ester, amide, clathrate, stereoisomer, enantiomer, prodrug or analog thereof, or a combination thereof. The isothiocyanatostilbene corresponds to the following formula:

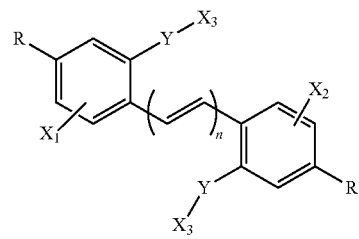

where $X_1$ is one H, F, Cl, $CF_3$, and $OCH_3$; $X_2$ is one H, F, Cl, $CF_3$, and $OCH_3$; n is a number value of carbon bond between two carbon atoms between parenthesize, and the number value is one of one, indicating a single bond, and two indicating a double bond; Y is one of $SO_2$ or S; each R is preferably N=C=S, but one or both may alternatively be one of, N=C=O, N=N—$OCH_3$, N=CH—$OCH_3$, $OCH_2OCH_3$, $OCOCCl_3$, and $OCOCF_3$, and the two Rs may be the same or different groups, and; the $X_3$s correspond to one of the following formulas, where the two $X_3$s may be the same or different formulas:

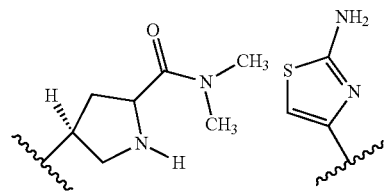

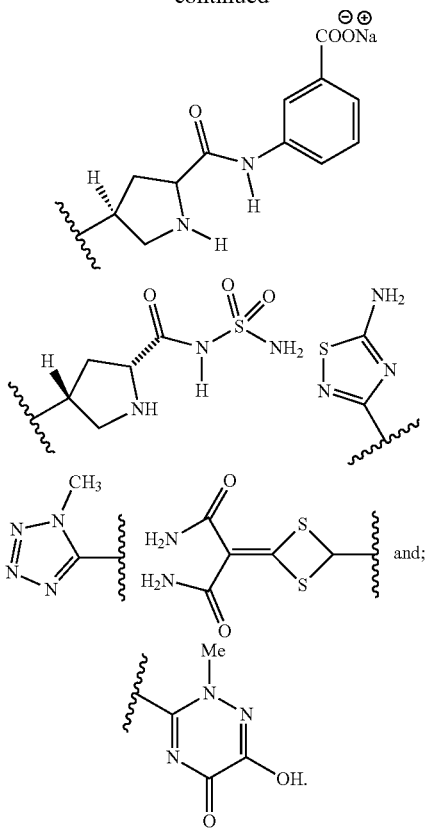

As used herein, the term "active agent" includes the one of the isothiocyanatostilbenes as described herein, including 4,4'-Diisothiocyanatostilbene-2,2'-disulfonic acid (DIDS), 4,4'-Diisothiocyanatodihydrostilbene-2,2'-disulfonic acid (H2DIDS), 4-acetamido-4'-isothiocyanatostilbene-2,2'-disulfonic acid (SITS), and 4,4'-dinitrostilbene-2,2'-disulfonic acid (DNDS). The term active agent may also be referred to as the active compound, active ingredient, active material, the inventive compound and/or the active drug substance.

As used herein, the term "delayed release" includes a pharmaceutical preparation, e.g., an orally administered formulation, which passes through the stomach substantially intact and dissolves in the small and/or large intestine (e.g., the colon). In some embodiments, delayed release of the active results from the use of an enteric coating of an oral medication (e.g., an oral dosage form).

The term an "effective amount" of an agent, as used herein, includes that amount sufficient to effect beneficial or desired results, such as clinical results, and, as such, an "effective amount" depends upon the context in which it is being applied.

The terms "extended release" or "sustained release" interchangeably includes a drug formulation that provides for gradual release of a drug over an extended period of time, e.g., 6-12 hours or more, compared to an immediate release formulation of the same drug. Preferably, although not necessarily, extended release results in substantially constant blood levels of a drug over an extended time period that are within therapeutic levels and fall within a peak plasma concentration range that is between, for example, 0.05-10 µM, 0.1-10 µM, 0.1-5.0 µM, or 0.1-1 µM.

As used herein, the terms "formulated for enteric release" and "enteric formulation" include pharmaceutical compositions, e.g., oral dosage forms, for oral administration able to provide protection from dissolution in the high acid (low pH) environment of the stomach. Enteric formulations can be obtained by, for example, incorporating into the pharmaceutical composition a polymer resistant to dissolution in gastric juices. In some embodiments, the polymers have an optimum pH for dissolution in the range of approx. 5.0 to 7.0 ("pH sensitive polymers"). Exemplary polymers include methacrylate acid copolymers that are known by the trade name Eudragit® (e.g., Eudragit® L100, Eudragit® S100, Eudragit® L-30D, Eudragit® FS 30D, and Eudragit® L100-55), cellulose acetate phthalate, cellulose acetate trimellitiate, polyvinyl acetate phthalate (e.g., Coateric®), hydroxyethylcellulose phthalate, hydroxypropyl methylcellulose phthalate, or shellac, or an aqueous dispersion thereof. Aqueous dispersions of these polymers include dispersions of cellulose acetate phthalate (Aquateric®) or shellac (e.g., MarCoat 125 and 125N). An enteric formulation reduces the percentage of the administered dose released into the stomach by at least 50%, 60%, 70%, 80%, 90%, 95%, or even 98% in comparison to an immediate release formulation. Where such a polymer coats a tablet or capsule, this coat is also referred to as an "enteric coating."

The term "immediate release," as used herein, includes that the agent (e.g., an isothiocyanatostilbene, or any pharmacologically acceptable salt, solvate, ester, amide, clathrate, stereoisomer, enantiomer, prodrug, or analog thereof, or a combination thereof), as formulated in a unit dosage form, has a dissolution release profile under in vitro conditions in which at least 55%, 65%, 75%, 85%, or 95% of the agent is released within the first two hours of administration to, e.g., a human. Desirably, the agent formulated in a unit dosage has a dissolution release profile under in vitro conditions in which at least 50%, 65%, 75%, 85%, 90%, or 95% of the agent is released within the first 30 minutes, 45 minutes, or 60 minutes of administration.

The term "pharmaceutical composition," as used herein, includes a composition containing an active agent described herein (e.g., an isothiocyanatostilbene, or any pharmacologically acceptable salt, solvate, ester, amide, clathrate, stereoisomer, enantiomer, prodrug, or analog thereof, or a combination thereof), formulated with a pharmaceutically acceptable excipient, and typically manufactured or sold with the approval of a governmental regulatory agency as part of a therapeutic regimen for the treatment of disease in a mammal, especially with the mammal being a human. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable excipient," as used herein, includes an ingredient other than the active agents described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, maltose, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "pharmaceutically acceptable prodrugs" as used herein, includes those prodrugs of the compounds of the present invention which are, within the scope of sound medical judgment, suitable for use in contact with the tissues of humans and animals with undue toxicity, irritation, allergic response, and the like, commensurate with a reasonable benefit/risk ratio, and effective for their intended use, as well as the zwitterionic forms, where possible, of the compounds of the invention.

The term "pharmaceutically acceptable salt," as use herein, includes those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. The salts can be prepared in situ during the final isolation and purification of the compounds of the invention or separately by reacting the free base group with a suitable organic or inorganic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The terms "pharmaceutically acceptable solvate" or "solvate," as used herein, includes a compound of the invention wherein molecules of a suitable solvent are incorporated in the crystal lattice. A suitable solvent is physiologically tolerable at the administered dose. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

The term "prevent," as used herein, includes prophylactic treatment or treatment that prevents one or more symptoms or conditions of a disease, disorder, or conditions described herein (e.g., cancer), or may refer to a treatment of a pre-disease state. Treatment can be initiated, for example, prior to ("pre-exposure prophylaxis") or following ("post-exposure prophylaxis") an event that precedes the onset of the disease, disorder, or conditions. Treatment that includes administration of a compound of the invention, or a pharmaceutical composition thereof, can be acute, short-term, or chronic. The doses administered may be varied during the course of preventive treatment.

The term "prodrug," as used herein, includes compounds which are rapidly transformed in vivo to the parent compound of the above formula. Prodrugs also encompass bioequivalent compounds that, when administered to a human, lead to the in vivo formation of an isothiocyanatostilbene, or any pharmacologically acceptable salt, solvate, ester, amide, clathrate, stereoisomer, enantiomer, prodrug, or analog thereof, or a combination thereof.

As used herein, and as well understood in the art, "treatment" includes an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e. not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Treatment" can also mean prolonging survival as compared to expected survival if not receiving treatment. As used herein, the terms "treating" and "treatment" can also refer to delaying the onset of, impeding or reversing the progress of, or alleviating either the disease or condition to which the term applies, or one or more symptoms of such disease or condition.

The term "unit dosage forms" includes physically discrete units suitable as unitary dosages for human subjects and other mammals, each unit containing a predetermined quantity of active material calculated to produce the desired therapeutic effect, in association with any suitable pharmaceutical excipient or excipients.

The present compounds can be prepared from readily available starting materials using the methods and procedures known in the art. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one of ordinary skill in the art by routine optimization procedures.

Pharmaceutical Compositions:

The methods described herein can also include the administrations of pharmaceutically acceptable compositions that include the isothiocyanatostilbenes, or any pharmacologically acceptable salt, solvate, ester, amide, clathrate, stereoisomer, enantiomer, prodrug, or analog thereof, or a combination thereof. Pharmaceutical compositions and dosage forms of the invention comprise one or more active ingredients in relative amounts and formulated so that a given pharmaceutical composition or dosage form inhibits cancer cell proliferation or other disease or condition where inhibiting the hepatocyte growth factor receptor can therapeutically influence the respective disease or condition progression. Preferred pharmaceutical compositions and dosage forms comprise an isothiocyanatostilbene, or any pharmacologically acceptable salt, solvate, ester, amide, clathrate, stereoisomer, enantiomer, prodrug, or analog thereof, or a combination thereof, optionally in combination with one or more additional active agents. When employed as pharmaceuticals, any of the present active agents can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration.

This invention also includes pharmaceutical compositions which can contain one or more pharmaceutically acceptable carriers. In making the pharmaceutical compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, powders, lozenges, sachets, cachets, elixirs, suspensions, emulsions, solutions, syrups, and soft and hard gelatin capsules. As is known in the art, the type of diluent can vary depending upon the intended route of administration. The resulting compositions can include additional agents, such as preservatives.

The therapeutic agents of the invention (e.g. the isothiocyanatostilbenes, or any pharmacologically acceptable salt, solvate, ester, amide, clathrate, stereoisomer, enantiomer, prodrug, or analog thereof, or a combination thereof) can be administered alone, combined, or in a mixture, in the presence of a pharmaceutically acceptable excipient or carrier. The excipient or carrier is selected on the basis of the mode and route of administration. Suitable pharmaceutical carriers, as well as pharmaceutical necessities for use in pharmaceutical formulations, are described in *Remington: The Science and Practice of Pharmacy*, 21$^{st}$ Ed., Gennaro, Ed., Lippencott Williams & Wilkins (2005), a well-known reference text in this field, and in the USP/NF (United States Pharmacopeia and the National Formulary). In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. Other exemplary excipients are described in *Handbook of Pharmaceutical Excipients*, 6$^{th}$ Edition, Rowe et al., Eds., Pharmaceutical Press (2009).

The pharmaceutical compositions can be formulated so as to provide immediate, extended, or delayed release of the active ingredient after administration to the patient by employing procedures known in the art.

The pharmaceutical compositions can be formulated in a unit dosage form, each dosage containing, e.g., 0.1-500 mg of the active ingredient. For example, the dosages can contain from about 0.1 mg to about 50 mg, from about 0.1 mg to about 40 mg, from about 0.1 mg to about 20 mg, from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg, from about 0.5 mg to about 20 mg, from about 0.5 mg to about 10 mg, from about 0.5 mg to about 5 mg; from about 1 mg from to about 50 mg, from about 1 mg to about 30 mg, from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 50 mg to about 100 mg of the active ingredient, from about 50 mg to about 300 mg, from about 50 mg to about 250 mg, from about 100 mg to about 300 mg, or, from about 100 mg to about 250 mg of the active ingredient. For preparing solid compositions such as tablets, the active agent may be mixed with one or more pharmaceutical excipients to form a solid bulk formulation composition containing a homogeneous mixture of a compound of the present invention. When referring to these bulk formulation compositions as homogeneous, the active ingredient is typically dispersed evenly throughout the composition so that the composition can be readily subdivided into equally effective unit dosage forms such as tablets and capsules. This solid bulk formulation is then subdivided into unit dosage forms of the type described above containing from, for example, 0.1 to about 500 mg of the active ingredient of the present invention.

Compositions for Oral Administration.

The pharmaceutical compositions contemplated by the invention include those formulated for oral administration ("oral dosage forms"). Oral dosage forms can be, for example, in the form of tablets, capsules, a liquid solution or suspension, a powder, or liquid or solid crystals, which contain the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Formulations for oral administration may also be presented as chewable tablets, as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Controlled release compositions for oral use may be constructed to release the active agent by controlling the dissolution and/or the diffusion of the active agent substance. Any of a number of strategies can be pursued in order to obtain controlled release and the targeted plasma concentration vs time profile. In one example, controlled release is obtained by appropriate selection of various formulation parameters and ingredients, including, e.g., various types of controlled release compositions and coatings. Thus, the administered therapeutic or drug is formulated with appropriate excipients into a pharmaceutical composition that, upon administration, releases the drug in a controlled manner. Examples include single or multiple unit tablet or capsule compositions, oil solutions, suspensions, emulsions, microcapsules, microspheres, nanoparticles, patches, and liposomes. In certain embodiments, compositions include biodegradable, pH, and/or temperature-sensitive polymer coatings.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions suitable for oral mucosal administration (e.g., buccal or sublingual administration) include tablets, lozenges, and pastilles, where the active ingredient is formulated with a carrier, such as sugar, acacia, tragacanth, or gelatin and glycerine.

Coatings:

The pharmaceutical compositions formulated for oral delivery, such as tablets or capsules of the present invention can be coated or otherwise compounded to provide a dosage form affording the advantage of delayed or extended release. The coating may be adapted to release the active agent in a predetermined pattern (e.g., in order to achieve a controlled release formulation) or it may be adapted not to release the active agent until after passage of the stomach, e.g., by use of an enteric coating (e.g., polymers that are pH-sensitive ("pH controlled release"), polymers with a slow or pH-dependent rate of swelling, dissolution or erosion ("time-controlled release"), polymers that are degraded by enzymes ("enzyme-controlled release" or "biodegradable release") and polymers that form firm layers that are destroyed by an increase in pressure ("pressure-controlled release")). Exemplary enteric coatings that can be used in the pharmaceutical compositions described herein include sugar coatings, film coatings (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or coatings based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose. Furthermore, a time delay material such as, for example, glyceryl monostearate or glyceryl distearate, may be employed.

For example, the tablet or capsule can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release.

When an enteric coating is used, desirably, a substantial amount of the active agent is released in the lower gastrointestinal tract.

In addition to coatings that effect delayed or extended release, the solid tablet compositions may include a coating adapted to protect the composition from unwanted chemical changes (e.g., chemical degradation prior to the release of the active agent). The coating may be applied on the solid dosage form in a similar manner as that described in *Encyclopedia of Pharmaceutical Technology*, vols. 5 and 6, Eds. Swarbrick and Boyland, 2000.

Parenteral Administration:

Within the scope of the present invention are also parenteral depot systems from biodegradable polymers. These systems are injected or implanted into the muscle or subcutaneous tissue and release the incorporated active agent over extended periods of time, ranging from several days to several months. Both the characteristics of the polymer and the structure of the device can control the release kinetics which can be either continuous or pulsatile. Polymer-based parenteral depot systems can be classified as implants or microparticles. The former are cylindrical devices injected into the subcutaneous tissue whereas the latter are defined as spherical particles in the range of 10-100 μm. Extrusion, compression or injection molding are used to manufacture implants whereas for microparticles, the phase separation method, the spray-drying technique and the water-in-oil-in-water emulsion techniques are frequently employed. The most commonly used biodegradable polymers to form microparticles are polyesters from lactic and/or glycolic acid, e.g. poly(glycolic acid) and poly(L-lactic acid) (PLG/PLA microspheres). Of particular interest are in situ forming depot systems, such as thermoplastic pastes and gelling systems formed by solidification, by cooling, or due to the sol-gel transition, cross-linking systems and organogels formed by amphiphilic lipids. Examples of thermosensitive polymers used in the aforementioned systems include, N-isopropylacrylamide, poloxamers (ethylene oxide and propylene oxide block copolymers, such as poloxamer 188 and 407), poly(N-vinyl caprolactam), poly(siloethylene glycol), polyphosphazenes derivatives and PLGA-PEG-PLGA.

Mucosal Drug Delivery:

Mucosal drug delivery (e.g., drug delivery via the mucosal linings of the nasal, rectal, vaginal, ocular, or oral cavities) can also be used in the methods described herein. Methods for oral mucosal drug delivery include sublingual administration (via mucosal membranes lining the floor of the mouth), buccal administration (via mucosal membranes lining the cheeks), and local delivery (Harris et al., *Journal of Pharmaceutical Sciences,* 81(1): 1-10, 1992)

Oral transmucosal absorption is generally rapid because of the rich vascular supply to the mucosa and allows for a rapid rise in blood concentrations of the therapeutic or active agent ("American Academy of Pediatrics: Alternative Routes of Drug Administration—Advantages and Disadvantages (Subject Review)," *Pediatrics,* 100(1):143-152, 1997).

For buccal administration, the compositions may take the form of, e.g., tablets, lozenges, etc. formulated in a conventional manner. Permeation enhancers can also be used in buccal drug delivery. Exemplary enhancers include 23-lauryl ether, aprotinin, azone, benzalkonium chloride, cetylpyridinium chloride, cetyltrimethylammonium bromide, cyclodextrin, dextran sulfate, lauric acid, lysophosphatidylcholine, methol, methoxysalicylate, methyloleate, oleic acid, phosphatidylcholine, polyoxyethylene, polysorbate 80, sodium EDTA, sodium glycholate, sodium glycodeoxycholate, sodium lauryl sulfate, sodium salicylate, sodium taurocholate, sodium taurodeoxycholate, sulfoxides, and alkyl glycosides. Bioadhesive polymers have extensively been employed in buccal drug delivery systems and include cyanoacrylate, polyacrylic acid, hydroxypropyl methylcellulose, and poly methacrylate polymers, as well as hyaluronic acid and chitosan.

Liquid drug formulations (e.g., suitable for use with nebulizers and liquid spray devices and electrohydrodynamic (EHD) aerosol devices) can also be used. Other methods of formulating liquid drug solutions or suspension suitable for use in aerosol devices are known to those of skill in the art.

Formulations for sublingual administration can also be used, including powders and aerosol formulations. Exemplary formulations include rapidly disintegrating tablets and liquid-filled soft gelatin capsules.

Dosing Regimens:

The present methods for treating cancer are carried out by administering one or more isothiocyanatostilbenes, or any pharmacologically acceptable salt, solvate, ester, amide, clathrate, stereoisomer, enantiomer, prodrug, or analog thereof, or a combination thereof for a time and in an amount sufficient to result in stabilization and/or reversal of cancer symptoms, or other disease or condition where inhibiting the hepatocyte growth factor receptor can therapeutically influence the respective disease or condition progression. The amount and frequency of administration of the compositions can vary depending on, for example, what is being administered, the state of the patient, and the manner of administration. The dosage is likely to depend on such variables as the type and extent of progression of the cancer, the severity of the cancer, the age, weight and general condition of the particular patient, the relative biological efficacy of the composition selected, formulation of the excipient, the route of administration, and the judgment of the attending clinician. Effective doses can be extrapolated from dose-response curves derived from in vitro or animal model test system. An effective dose is a dose that produces a desirable clinical outcome by, for example, improving a sign or symptom of cancer or slowing its progression.

The amount of active agent per dose can vary. For example, a subject can receive from about 0.1 µg/kg to about 10,000 µg/kg. Generally, the active agent is administered in an amount such that the peak plasma concentration ranges from 150 nM-250 µM.

Exemplary dosage amounts can fall between 0.1-5000 µg/kg, 100-1500 µg/kg, 100-350 µg/kg, 340-750 µg/kg, or 750-1000 µg/kg. Exemplary dosages can 0.25, 0.5, 0.75, 1°, or 2 mg/kg. In another embodiment, the administered dosage can range from 0.05-5 mmol of an active agent (e.g., 0.089-3.9 mmol) or 0.1-50 µmol of an active agent (e.g., 0.1-25 µmol or 0.4-20 µmol).

The frequency of treatment may also vary. The subject can be treated one or more times per day with the active agent (e.g., once, twice, three, four or more times) or every so-many hours (e.g., about every 2, 4, 6, 8, 12, or 24 hours). Preferably, the pharmaceutical composition is administered 1 or 2 times per 24 hours. The time course of treatment may be of varying duration, e.g., for two, three, four, five, six, seven, eight, nine, ten or more days. For example, the treatment can be twice a day for three days, twice a day for seven days, twice a day for ten days. Treatment cycles can be repeated at intervals, for example weekly, bimonthly or monthly, which are separated by periods in which no treatment is given. The treatment can be a single treatment or can last as long as the life span of the subject (e.g., many years).

KITS: Any of the pharmaceutical compositions of the invention described herein can be used together with a set of instructions, i.e., to form a kit. The kit may include instructions for use of the pharmaceutical compositions as a therapy as described herein. For example, the instructions may provide dosing and therapeutic regimes for use of the compounds of the invention to reduce incidence, duration, and or severity of cancer, cell proliferation disorder, or other disease or condition where inhibiting the hepatocyte growth factor receptor can influence the respective disease or condition progression.

Various objects, features, aspects, and advantages of the present invention will become more apparent from the following detailed description of preferred embodiments of the invention, along with the accompanying drawings in which like numerals represent like components. The present invention may address one or more of the problems and deficiencies of the current technology discussed above. However, it is contemplated that the invention may prove useful in addressing other problems and deficiencies in a number of technical areas. Therefore the claimed invention should not necessarily be construed as limited to addressing any of the particular problems or deficiencies discussed herein.

BRIEF DESCRIPTION OF THE DRAWINGS

The accompanying drawings, which are incorporated in and constitute a part of the specification, illustrate various embodiments of the invention and together with the general description of the invention given above and the detailed description of the drawings given below, serve to explain the principles of the invention. It is to be appreciated that the accompanying drawings are not necessarily to scale since the emphasis is instead placed on illustrating the principles of the invention. The invention will now be described, by way of example, with reference to the accompanying drawings in which:

FIG. 1a is the Molecular structures of stilbene compounds examined. All compounds share the same backbone, except H2DIDS which is lacking a double bond, indicated by a red arrow. Three of the four compounds contain at least one isothiocyanate group, indicated by blue boxes.

FIGS. 3A-3D are a set of nine photographs and three graphs showing DIDS and H2DIDS reduce HGF-induced but not EGF-induced cell scattering and wound healing. FIG. 3A shows images of DU145 cells that were treated with 33 ng/ml HGF or 100 ng/ml EGF overnight in the presence of 4 μM DIDS or 25 μM H2DIDS. Cells were fixed and stained for actin. Representative images are shown. FIGS. 3B-3D shows where confluent monolayers of DU145 cells were wounded prior to treatment with 33 ng/ml HGF or 100 ng/ml EGF for the indicated times in the presence of 4 μM DIDS or 25 μM H2DIDS. Data are shown as mean±S.E.M.; n=3.

FIGS. 5A-5B are two bar graphs and two sets of six images depicting that stilbene compounds reduce 3D spheroid growth. DU145 spheroids suspended in Matrigel were treated with DIDS (FIG. 5A) or H2DIDS (FIG. 5B) in the presence of 33 ng/mL HGF for 72 hours; n=3. Data are shown as the percent change in growth from T=0 to T=72 hours. For each of the six independent variables in each bar graph, a representative image at the 72 hour time point is shown. The six corresponding images below each respective bar graph FIG. 6C shows H1993 cells that were treated with 5 μM SU11274, 5 μM DIDS, 5 μM H2DIDS, or serum-free media for the indicated times; n=3. Western blot was used to analyze pMet expression.

FIG. 7A shows body weight of treated mice measured throughout the duration of the experiment. FIG. 7B shows caliper measurements taken on the indicated days and average tumor volume calculated. FIG. 7C shows average mass of tumors harvested at the end of the experiment. Data are shown as average+S.E.M., *p<0.05.

FIG. 8C shows HCC1806 cells that were treated similarly except 12.5 μM-100 μM H2DIDS is shown. Western blot was used to analyze the indicated proteins. Densitometry shows changes in pMet compared to HGF control normalized to 1.

DETAILED DESCRIPTION OF THE INVENTION

Figure 1B:
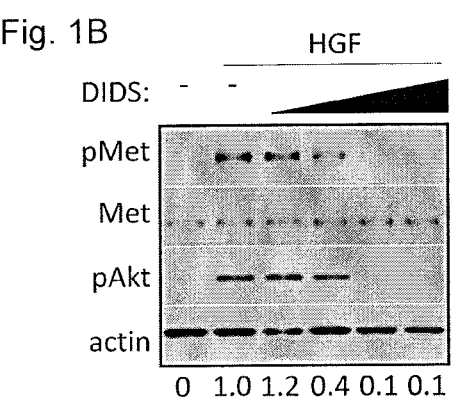
FIGS. 1B-1E are photographs of Western blot analysis of respective stilbene compounds showing reduction of c-Met activation in a dose-dependent manner. Results are shown of DU145 cells treated with 33 ng/ml HGF for 20 minutes in the presence of 500 nM, 2 uM, 8 uM, 32 uM DIDS (FIG. 1B) or H2DIDS (FIG. 1C), 125 uM, 250 uM, 500 uM, 1 mM SITS (FIG. 1D), or 250 uM, 500 uM, 1 mM, 2 mM DNDS (FIG. 1E). Densitometry shows changes in pMet compared to HGF control normalized to 1.
Figure 1C:
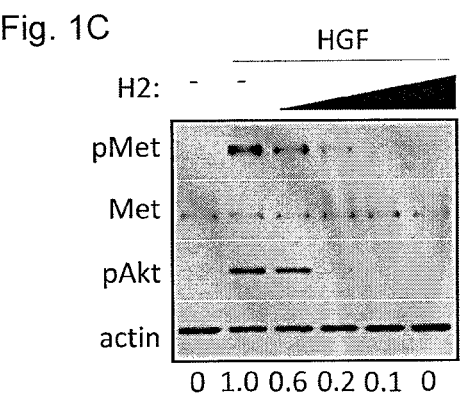
Figure 1D:
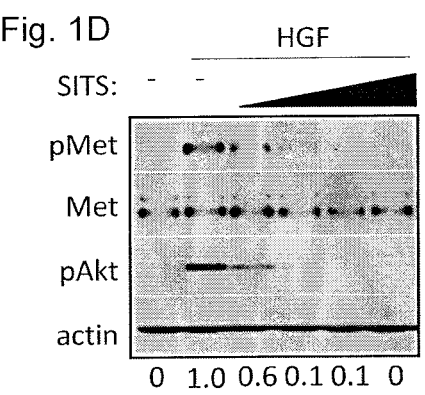
Figure 1E:
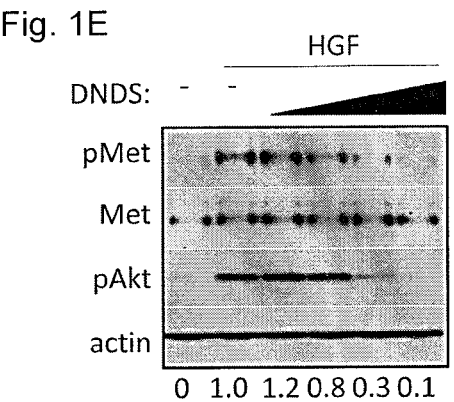

The present invention will be understood by reference to the following detailed description, which should be read in conjunction with the appended drawings. It is to be appreciated that the following detailed description of various embodiments is by way of example only and is not meant to limit, in any way, the scope of the present invention. In the summary above, in the following detailed description, in the claims below, and in the accompanying drawings, reference is made to particular features (including method steps) of the present invention. It is to be understood that the disclosure of the invention in this specification includes all possible combinations of such particular features, not just those explicitly described. For example, where a particular feature is disclosed in the context of a particular aspect or embodiment of the invention or a particular claim, that feature can also be used, to the extent possible, in combination with and/or in the context of other particular aspects and embodiments of the invention, and in the invention generally. The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)–(a second number)," this means a range whose lower limit is the first number and whose upper limit is the second number. For example, 25 to 100 mm means a range whose lower limit is 25 mm, and whose upper limit is 100 mm. The embodiments set forth the below represent the necessary information to enable those skilled in the art to practice the invention and illustrate the best mode of practicing the invention. In addition, the invention does not require that all the advantageous features and all the advantages need to be incorporated into every embodiment of the invention.

Figure 8A:
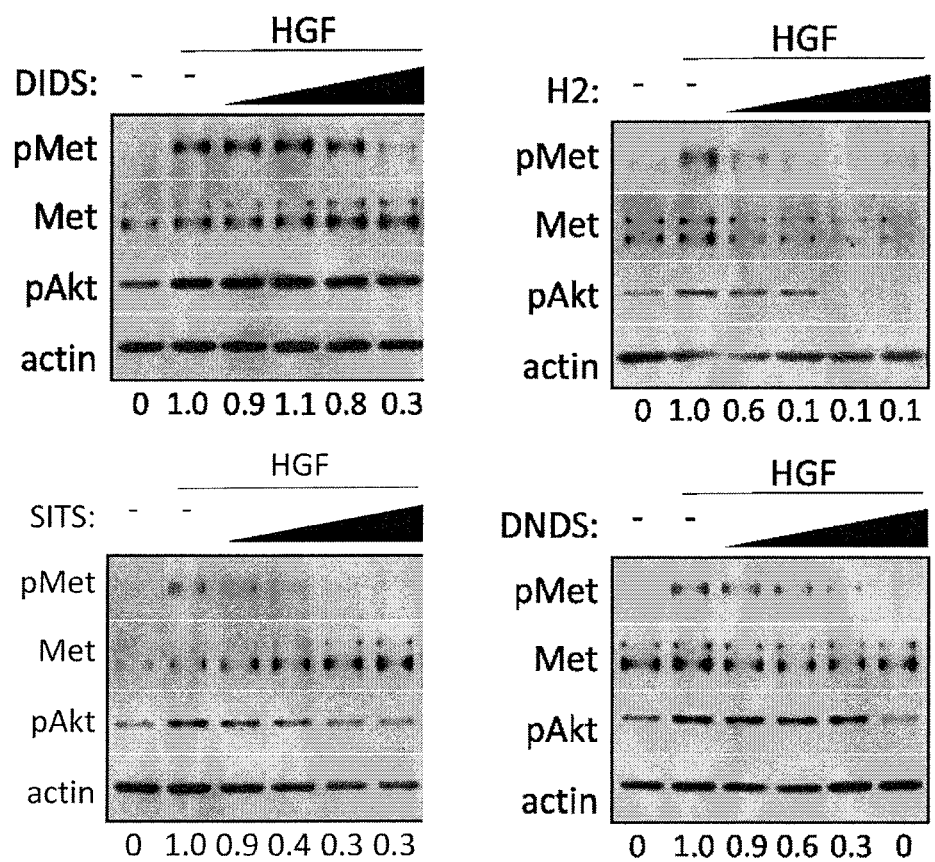
FIGS. 8A-8C are twelve photographs of Western blot analyses showing that stilbene compounds reduce c-Met activation at similar concentrations in multiple cell lines. PC3 prostate cancer (shown in FIG. 8A) and MDA-MB-231 breast cancer (shown in FIG. 8B) cells were treated with 33 ng/ml HGF for 20 minutes serum-free media in the presence of 500 nM-4 μM DIDS, 500 nM-32 μM H2DIDS, 125 μM-1 mM SITS, or 250 μM-2 mM DNDS.
Figure 8B:
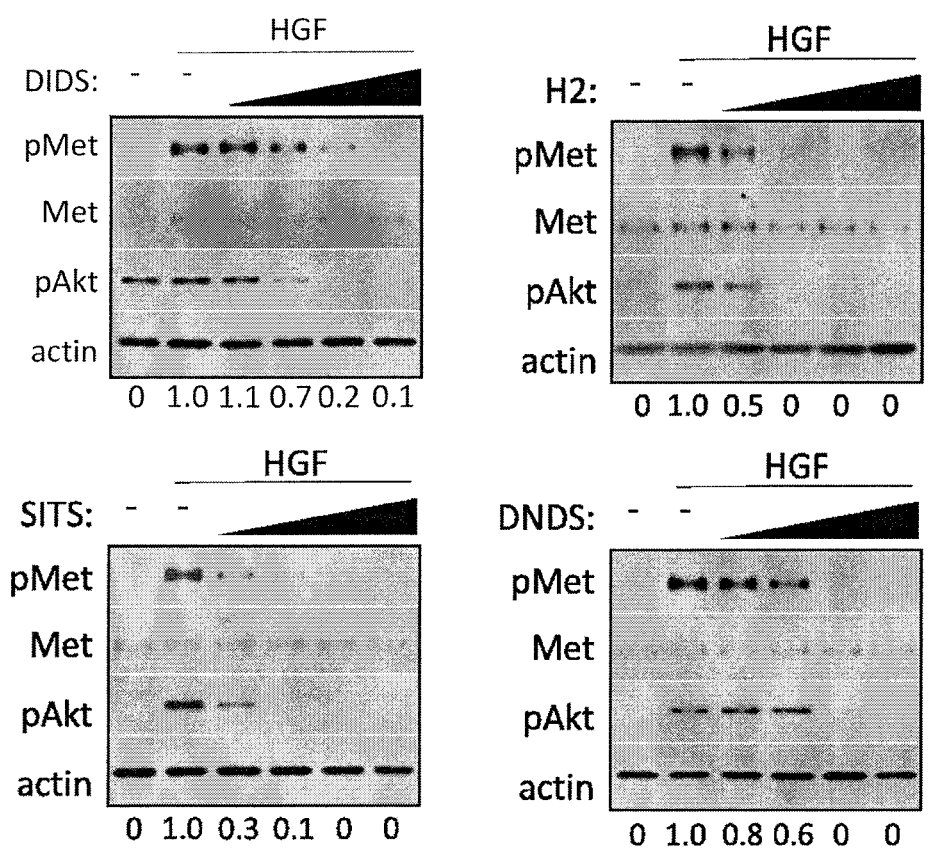
Figure 8C:
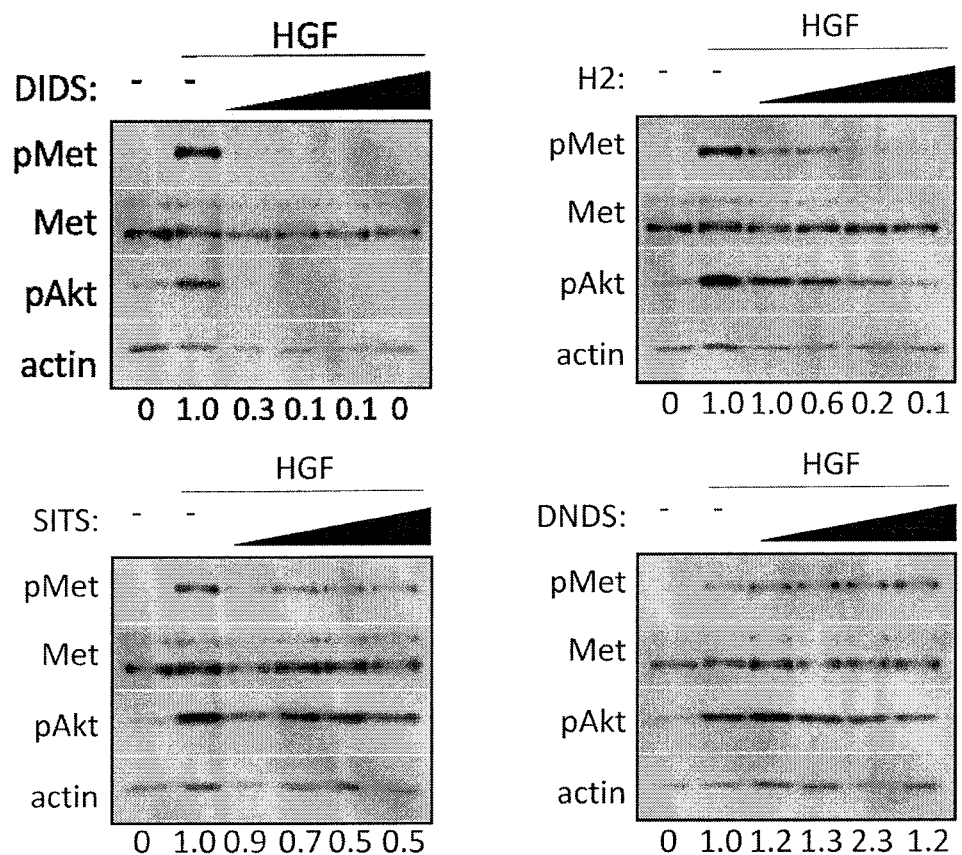
Figure 9A:
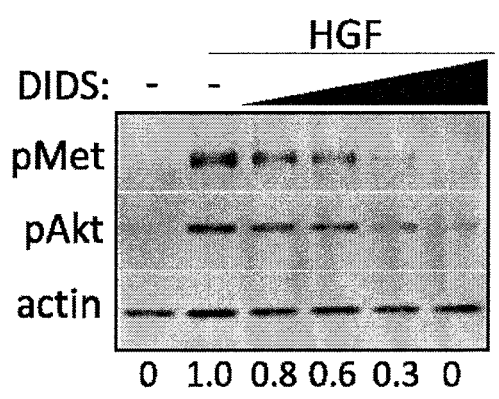
FIGS. 9A-9B are two photographs of Western blot analyses showing that compounds reduce c-Met activation at similar concentrations in complete media. DU145 cells were treated with DIDS (FIG. 9A) or H2DIDS (FIG. 9B) at 1.3 μM, 3.8 μM, 11.3 μM, or 33.8 μM in the presence of 33 ng/ml HGF for 20 minutes in 10% FBS RPMI. Western blot was used to analyze the indicated proteins.
Figure 9B:
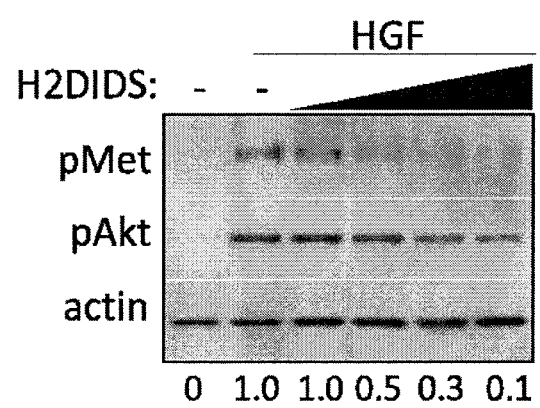

Turning now to FIG. 1, a brief description concerning the various components of the present invention will now be briefly discussed. The inventors discovered that isothiocyanatostilbenes reduce c-Met phosphorylation: While using DIDS as an inhibitor of anion exchangers, by happenstance, the inventors discovered DIDS impacted c-Met phosphorylation. Importantly, DIDS reduced activation of c-Met at concentrations that were too low to inhibit anion exchangers. This indicated that DIDS acts as a c-Met inhibitor independent of its ability to target anion transport. The ability of DIDS to inhibit c-Met activation at a reasonably low concentration evidence that DIDS and other stilbene analogs are potential clinical therapeutics. The inventors subsequently obtained additional stilbene compounds, H2DIDS, SITS, and DNDS, to assess their structure activity relationship. These compounds have similar structural scaffolds and differ in the number of isothiocyanate substituent groups (FIG. 1a). DNDS is structurally similar, but the two isothiocyanate substituents were replaced by nitro groups. Notably, H2DIDS only differs from DIDS by its reduced two-carbon linker chain that connects both aromatic rings; therefore, H2DIDS is the dihydro analog of DIDS. Western blot analysis of a serum-free dose response curve in DU145 prostate cancer epithelial cells showed that ~8 µM DIDS reduced c-Met activation and downstream Akt by ~90% (FIG. 1b). FIGS. 1c-e show that H2DIDS, SITS and DNDS inhibited c-Met by ~90% at 8 µM, 250 µM and 2 mM, respectively. These compounds also exhibited similar, though not identical, effective doses in PC3 prostate cancer (FIG. 8a), MDA-MB-231 breast cancer (FIG. 8b), and HCC1806 breast cancer (FIG. 8c) cells. In all tested cell lines, DIDS and H2DIDS consistently demonstrated higher potencies for inhibiting c-Met activation by HGF; therefore, the inventors focused on these two compounds for the remaining duration of the study. The inventors found that DIDS and H2DIDS had slightly higher effective concentrations in dose response assays containing 10% FBS (FIGS. 9a and 9b).

Figure 2A:
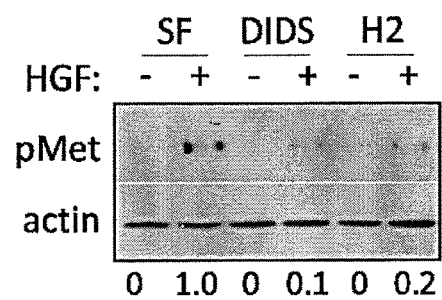
FIGS. 2A-2C are photographs of Western blot analysis of DIDS and H2DIDS showing reduction of c-Met activation, but not EGFR or IGFR. DU145 cells were treated with 33 ng/ml HGF (FIG. 2A), 100 ng/ml EGF (FIG. 2B), or 100 ng/ml IGF (FIG. 2C) for 20 minutes in the presence of 4 μM DIDS or 25 μM H2DIDS.

To begin to assess the specificity of DIDS and H2DIDS, the inventors treated DU145 cells with concentrations of DIDS and H2DIDS known to the inventors to inhibit c-Met activation in combination with HGF, epidermal growth factor (EGF), or insulin-like growth factor (IGF). Western blot analysis revealed that concentrations of DIDS and H2DIDS that reduce c-Met activation do not significantly reduce EGFR or IGFR activation (FIGS. 2a-c), suggesting some degree of selectivity for c-Met.

Figure 2B:
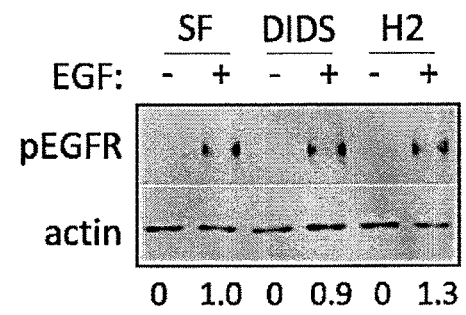
Figure 2C:
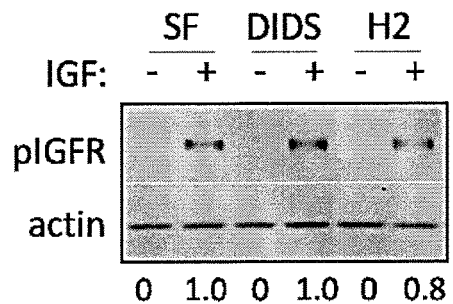
Figure 4A:
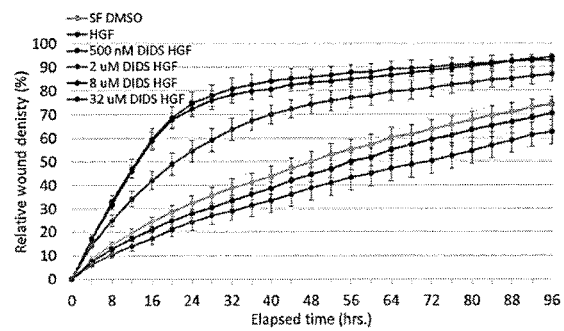
FIGS. 4A-4D are four graphs showing DIDS and H2DIDS reduce HGF-induced wound healing and invasion in a dose-dependent manner. DU145 cells were treated with the indicated concentrations of DIDS (FIGS. 4A and 4C) or H2DIDS (FIGS. 4B and 4D) in the presence of 33 ng/mL HGF. For invasion (FIGS. 4C and 4D), wounded cells were overlaid with Matrigel diluted 1:5 in serum-free media; n=3.
Figure 4B:
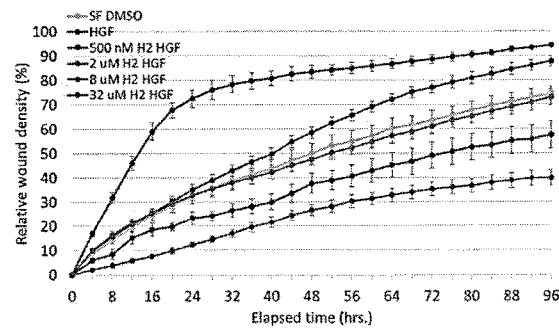
Figure 10:
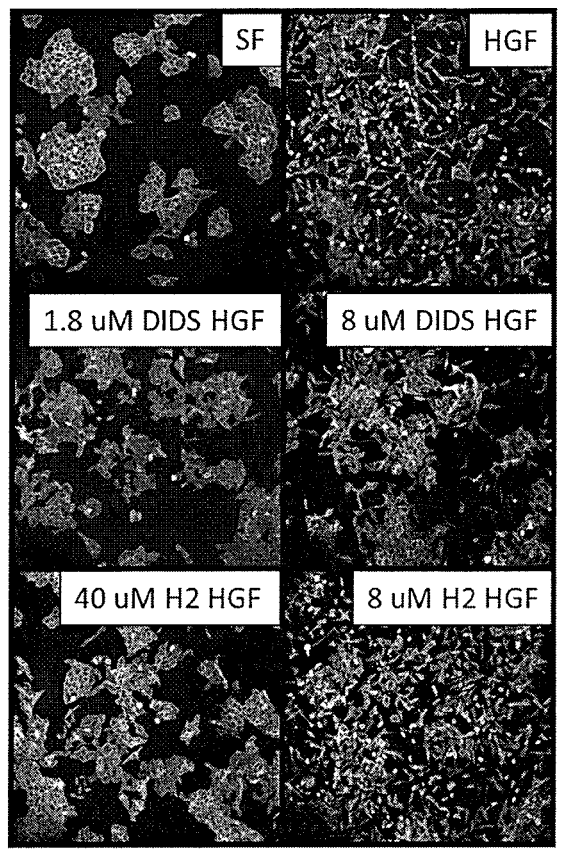
FIG. 10 is six photographs showing DIDS and H2DIDS dose response inhibition of HGF-induced cell scattering. DU145 cells were treated with 33 ng/ml HGF overnight in the presence of 1.8 μM or 8 μM DIDS and 8 μM or 40 μM H2DIDS. Cells were fixed and stained for actin. Representative images are shown.

DIDS and H2DIDS reduce HGF-induced cell motility and invasion: The inventors next sought to determine the effect of these compounds on HGF-mediated phenotypes. DU145 cells exhibit a striking scattered and motile phenotype in response to EGF and HGF stimulation indicative of an epithelial-mesenchymal transition. An initial dose response scattering assay revealed that DIDS inhibited HGF-induced scattering between 1.8 µM and 8 µM and H2DIDS was effective between 8 µM and 40 µM (FIG. 10). Using concentrations of DIDS and H2DIDS within this range, the inventors discovered that these same concentrations were able to reduce HGF-induced, but not EGF-induced cell scattering (FIG. 3a). This was consistent with the inventors' observations that DIDS and H2DIDS do not inhibit EGFR signaling (FIG. 2b). Similarly, HGF-induced wound healing, a unique collective form of cell motility, was also significantly reduced while the same concentrations had minimal effects on EGF-mediated wound healing (FIG. 3b-3d). The inventors further examined dose response effects of DIDS and H2DIDS on c-Met phenotypes. FIGS. 4a and 4b show that DIDS and H2DIDS reduce HGF-induced wound healing in a dose response manner.

Figure 4C:
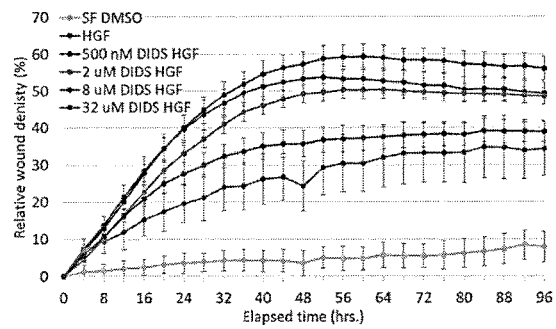
Figure 4D:
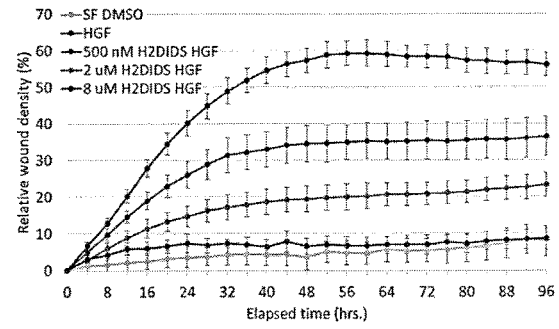
Figure 11A:
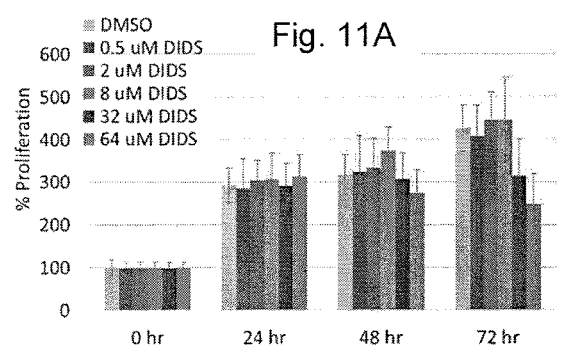
FIGS. 11A-11D are four bar graphs showing DIDS and H2DIDS have minimal effects on 2D cell proliferation. Cells were treated with the indicated concentrations of DIDS (FIGS. 11A and 11C) or H2DIDS (FIGS. 11B and 11D) in serum-free media (FIGS. 11A and 11B) or complete media (FIGS. 11C and 11D) for the indicated times; n=3.
Figure 11B:
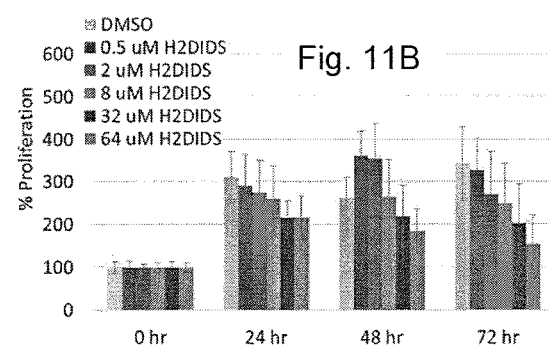
Figure 11C:
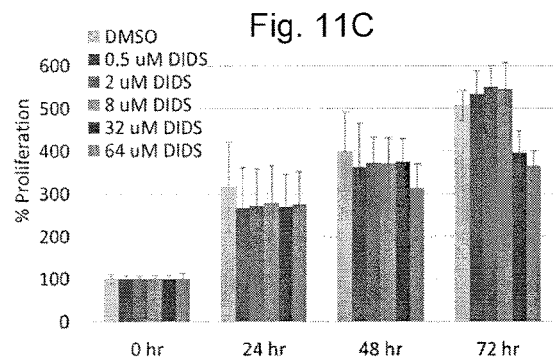
Figure 11D:
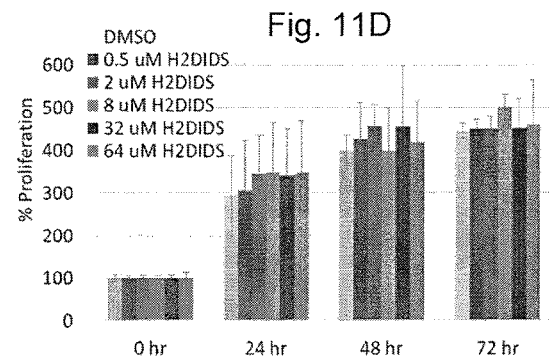

Similarly, these compounds inhibited HGF-induced invasion through Matrigel in a dose-dependent manner (FIGS. 4c and 4d). Although seemingly effective, the highest concentration of H2DIDS is not shown in FIG. 4d due to a consistent but anomalous precipitant or interaction of H2DIDS with the Matrigel that resulted in grainy images precluding accurate quantitative analysis. DIDS was able to inhibit wound healing more effectively than similar concentrations used to inhibit invasion. H2DIDS appeared to be slightly more effective than DIDS in wound healing and much more effective in invasion assays. Notably, these concentrations of DIDS and H2DIDS had minimal effects on serum-free proliferation (FIGS. 11a and 11b) and proliferation in complete media (FIGS. 11c and 11d) in a 2D assay. Collectively, these data evidence that DIDS and H2DIDS can negatively affect c-Met/HGF-induced cell motility and invasion, but not by affecting proliferation in 2D.

DIDS and H2DIDS decrease HGF-induced 3D spheroid proliferation: To better determine effective concentrations useful for in vivo applications, the inventors analyzed the effects of these stilbenes on cells grown in a 3D environment. For this assay, cells were embedded in Matrigel and treated concomitantly with DIDS or H2DIDS. Dose response curves showed that 5 µM DIDS and H2DIDS decreased HGF-induced DU145 spheroid growth by ~60% and still had some inhibitory effects as low as 40 nM (FIGS. 5a and 5b). These data suggest that DIDS and H2DIDS are effective in environments that more closely mimic in vivo conditions.

Figure 6A:
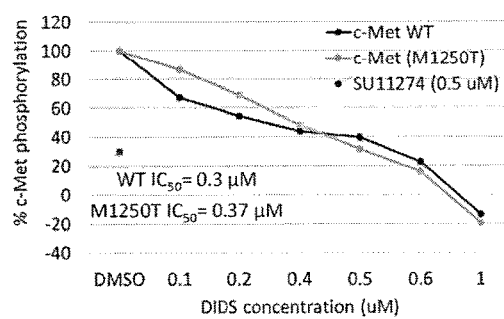
FIGS. 6A-6C are two line graphs and three photographs of Western blots showing that DIDS and H2DIDS inhibit and reverse c-Met phosphorylation. Inhibition of wild-type (WT) and mutant (M1250T) c-Met phosphorylation was examined using various concentrations of DIDS (FIG. 6A) or H2DIDS (FIG. 6B).
Figure 6B:
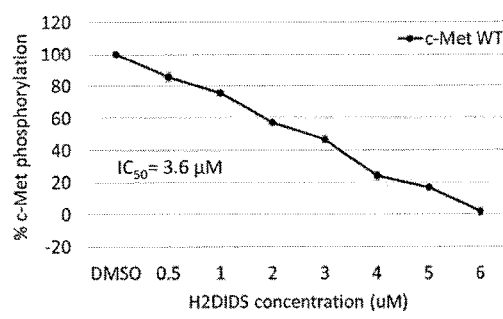

DIDS and H2DIDS inhibit and reverse c-Met phosphorylation: The inventors next determined the mechanism by which isothiocyanatostilbenes inhibit c-Met phosphorylation. SU11274 is a well-established class I c-Met inhibitor that competitively binds the ATP-binding site of c-Met. In order to determine if DIDS acts in a manner similar to a class I c-Met inhibitor, the inventors compared DIDS and H2DIDS to SU11274 in the following assays. First, ex vivo kinase assays were performed. At 500 nM, SU11274 reduced c-Met phosphorylation by ~70% and DIDS was found to reduce activation of wild-type c-Met with an $IC_{50}$ of 300 nM (FIG. 6a). H2DIDS was not as effective as DIDS, as the $IC_{50}$ for H2DIDS was 3.6 µM (FIG. 6b). The inventors also tested the ability of DIDS to inhibit c-Met M1250T (M1268T), a known mutant form of the receptor found in several types of cancers, including, for example, NSCLS, SCLC, hereditary papillary renal cell carcinoma, and gastric cancer, that can increase kinase activity and alter substrate specificity. DIDS inhibited this form of the receptor with an $IC_{50}$ of 370 nM (FIG. 6a).

Figure 6C:
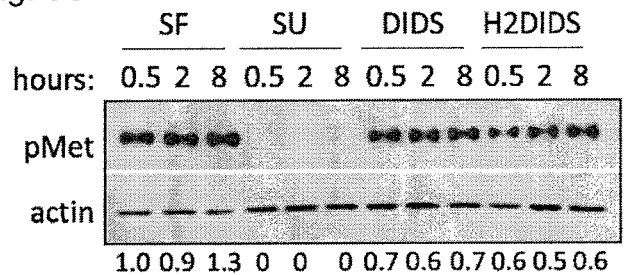

Although it appeared DIDS can act as an ATP-binding pocket inhibitor, the inventors further examined other possible mechanistic avenues. H1993 lung cancer cells were treated with DIDS, H2DIDS, and SU11274 prior to western blot analysis. H1993 cells have c-Met amplification such that they have high levels of pMet, even in the absence of HGF, due to constitutive c-Met dimerization and autophosphorylation. Interestingly, SU11274 ameliorated pMet levels in H1993 cells while DIDS and H2DIDS had much less significant effects (FIG. 6c). These data suggested that DIDS and H2DIDS act in a similar manner to SU11274 in their ability to inhibit c-Met kinase activity; however, SU11274 is able to ameliorate c-Met activation occurring independent of ligand-receptor interaction while DIDS and H2DIDS are much less effective.

Figure 6E:
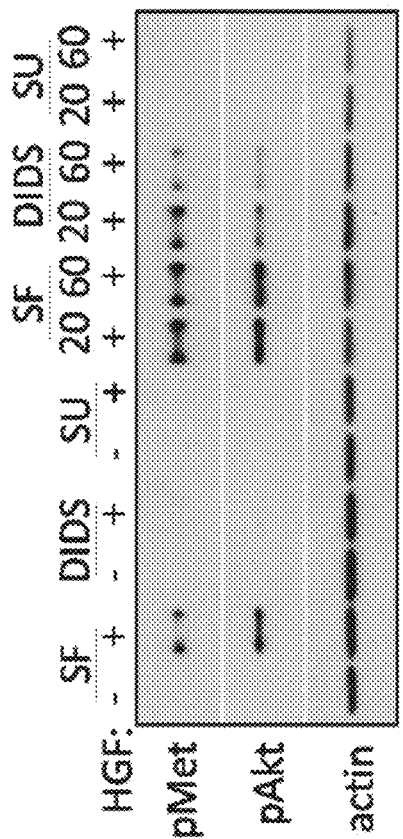
FIG. 6E shows DU145 cells that were treated with 33 ng/ml HGF for 20 minutes prior to washing followed by 4 μM DIDS or 10 μM SU11274 for 20 or 60 minutes. DIDS and SU11274 were HGF for 20 minutes as a control. Western blot was used to analyze the indicated proteins.
Figure 6D:
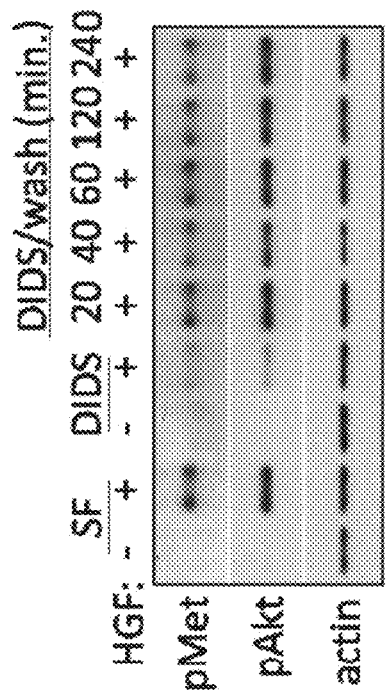
FIG. 6D shows DU145 cells that were treated with 4 μM DIDS for 20 minutes prior to washing for the indicated times followed by treatment with 33 ng/ml HGF for 20 minutes.

It has been reported that DIDS can exhibit covalent crosslinking properties. To determine if this could account for c-Met inhibition, the inventors treated DU145 cells with DIDS followed by one wash step and up to 1 hour recovery time prior to activation with HGF. Even as early as 20 minutes post-wash, HGF was able to activate c-Met to non-DIDS treated levels (FIG. 6d) suggesting DIDS does not irreversibly bind c-Met. Surprisingly, the inventors found that DIDS treatment post HGF treatment reduced pMet levels suggesting that DIDS is able to reverse c-Met activation under certain conditions (FIG. 6e). This is further supported by the inventors' data (FIG. 6d).

Figure 7A:
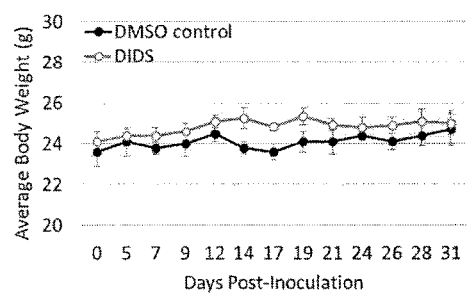
FIGS. 7A-7C are two line graphs and a bar graph showing DIDS is not toxic and appears to reduce tumor progression in vivo. Mice were treated with 5 mg/kg DIDS or equivalent volume DMSO for 14 days, followed by 10 mg/kg DIDS for an additional 16 days.
Figure 7B:
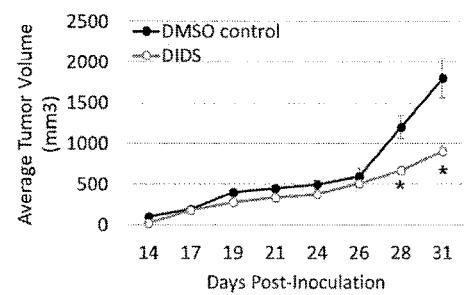
Figure 7C:
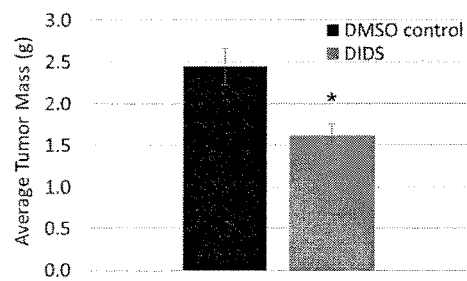

DIDS is well-tolerated in vivo: Since DIDS and H2DIDS were capable of inhibiting c-Met activation at relatively low concentrations and the inventors are not aware of any previous in vivo data on these compounds having been reported, the inventors performed a preliminary experiment in a mouse model of breast cancer to determine if DIDS could be tolerated in vivo. For ~2 weeks, mice were treated with 5 mg/kg DIDS delivered intraperitoneally. No obvious signs of toxicity were observed, so DIDS treatments were increased to 10 mg/kg for ~2 additional weeks. FIG. 7a shows that no change in body weight was observed in DIDS-treated mice compared to mice treated with dimethyl sulphoxide (DMSO) control. Tumors became palpable on day 14 and measurements taken via caliper showed DIDS began to reduce tumor size towards the end of the experiment (FIG. 7b). Differences in overall tumor weight were evident following necropsy (FIG. 7c). Because of the structural similarity of H2DIDS to DIDS, H2DIDS is expected to be similarly well-tolerated.

Discussion:

The accumulation of information implicating c-Met as a major regulator of tumor progression for a wide swath of cancers has and continues to drive the search for effective c-Met inhibitors for over 30 years. In the present disclosure, the inventors disclose the unexpected finding that isothiocyanatostilbenes are c-Met inhibitors. Notably, DIDS and H2DIDS have two isothiocyanate groups and were consistently more effective at c-Met inhibition than SITS, which has one isothiocyanate group while the other was replaced by an acetamido group, and DNDS, which has no isothiocyanate groups. Additionally, SITS was more effective at reducing c-Met phosphorylation than DNDS based on western blot analysis of multiple cancer cell lines (FIGS. 1 and 8). These data evidence that the isothiocyanate group is the principal bioactive moiety for c-Met inhibition.

Cell-free kinase assays suggested DIDS has a 300 nM $IC_{50}$ for c-Met kinase activity while H2DIDS has an $IC_{50}$ in the low micromolar range (FIGS. 3a and 3b). Additionally, DIDS and H2DIDS inhibited HGF-mediated phenotypes in various cell assays, but had minimal effects on EGF-mediated phenotypes (FIGS. 3-5). Finally, preliminary studies examining toxicity of DIDS in an animal model evidence that DIDS is well-tolerated in vivo and may be anti-tumorigenic, even in a tumor model not primarily driven by c-Met (FIG. 7). The inventors predict that future studies examining DIDS efficacy in a c-Met driven tumor model will show greater anti-tumorigenic efficacy. Thus, the data presented herein identify isothiocyanatostilbene analogs as novel c-Met inhibitory leads in multiple model systems.

Isothiocyanatostilbenes are known as anion transport inhibitors, although other roles for these compounds have been reported. Specifically, DIDS has been demonstrated to inhibit protein translocation across the ER membrane and inhibit matrix metalloproteinase release, both at concentrations of 400 µM and greater. At low micromolar concentrations, DIDS was found to prevent the interaction of human immunodeficiency virus type-1 (HIV-1) with CD4 T-cell receptors and reduce activity of succinic dehydrogenase and $F_0F_1$-ATP synthase.

Specificity is desirable in the clinic to ensure predictability, and the inventors' results found DIDS to be tolerable in mice and selective to c-Met over other tested receptor tyrosine kinases. Furthermore, of the two FDA-approved c-Met inhibitors, cabozantinib is prescribed with c-Met as the intended primary target; whereas crizotinib is prescribed based on ALK expression status. This highlights the lack of specific c-Met inhibitors approved for use, and that it is likely c-Met inhibitors with additional targets will prove more successful than specific inhibitors. Multi-kinase inhibitors can be effective at preventing the acquisition of resistance pathways, and c-Met signaling as a resistance pathway is amply reported throughout the literature, making it an important secondary target for therapy as well.

Interestingly, the inventors observed that DIDS targets $P_{2X}$, $P_{2Y}$, and $P_{2Z}$ receptors and recent large scale genetic screening data suggest that $P_{2Y}$ receptor signaling is one mechanism that contributes to resistance to ALK inhibitors, such as crizotinib. The reported information combined with the disclosed discovery c-Met inhibition by isothiocyanatostilbenes evidence that a combination therapy of crizotinib and DIDS would prevent $P_{2Y}$ ALK inhibitor resistance while enhancing c-Met inhibition, thus targeting two potential resistance pathways following crizotinib treatment. Additional therapeutic combinations are contemplated with one or more of the isothiocyanatostilbenes, or any pharmacologically acceptable salt, solvate, ester, amide, clathrate, stereoisomer, enantiomer, prodrug, or analog thereof, or a combination thereof and one or more other c-Met inhibitors including Crizotinib (PF-02341066), Cabozantinib (XL184, BMS-907351), Foretinib (GSK1363089), PHA-665752, SGX-523, BMS-777607, Tivantinib (ARQ 197), JNJ-38877605, PF-04217903, MGCD-265, Capmatinib (INCB28060), BMS-754807, BMS-794833, AMG-208, MK-2461, Golvatinib (E7050), AMG-458, Tepotinib (EMD 1214063), NVP-BVU972, NPS-1034, or any pharmacologically acceptable salt, solvate, ester, amide, clathrate, stereoisomer, enantiomer, prodrug, or analog thereof, or a combination thereof.

The present invention further includes a combination or formulation of an isothiocyanatostilbene, and a pharmacologically acceptable salt, solvate, ester, amide, clathrate, stereoisomer, enantiomer, prodrug or analog thereof, or a combination thereof, with one or more additional pharmaceutically active agents. The additional pharmaceutically active agents could include one or more or all of (1) an additional distinct isothiocyanatostilbene, (2) an agent that targets receptor tyrosine kinases (RTK), also called a receptor tyrosine kinase inhibitor (RTKi), (3) an agent that targets non receptor tyrosine kinases, and (4) an anti-cell proliferative chemotherapeutic agent, or of a pharmacologically acceptable salt, solvate, ester, amide, clathrate, stereoisomer, enantiomer, prodrug or analog thereof.

The RTK targeted by the RTKi agent could include one or more of c-Met, RON, ROS, EGFR1, EGFR2, EGFR3, EGFR4, EGRFvIII, c-Kit, c-FMS, FLT3, PDGFR, IGFR, VEGFR, VEGR2, TIE-1, TIE-2, PTK-7, FGFR1-3, TRKA-C, RORs, BCR-ABL, EPHA1-5, EPHB1-4, and RET. The RTKi agent could include one or more of Alectinib, Axitinib, Crizotinib, Cabozantinib, Centinib, Erlotinib, Gefitinib, Lapatinib, Lenvatinib, Osimertinib, Pazopanib, Ponatinib, Regorafenib, Sorafenib, Sunitinib, Tofacitinib, Vandetanib, and Vismodegib.

The agents that target non-receptor kinases may be an anti-cancer or anti-tumor agent. The non-receptor tyrosine kinases may include one or more of ABL1-2, ACK1, BLK, Bmx, bRAF, BRK, BTK, CSK, FAK, FES, FRK, FYNA, HCK, ITK, Jakl-2, LCK, Lok1, LRRK2, LYNA-B, MNK1, MEK, mTOR, PI3K, PYK2, Src, Syk, Zap-70, and CDK4. The non-receptor tyrosine kinase inhibitors may include one or more of Bosultinib, Cobimetinib, Dabrafenib, Dasatinib, Everolimus, Ibrutinib, Idelalisib, Imatinib, nilotinib, Palbociclib, Ponatinib, Rogorafenib, Ruxolitinib, Temsirolimus, and Trametinib.

The anti-cell proliferative chemotherapeutic agent may include one or more of anti-cancer and anti-tumor drugs. The anti-cell proliferative chemotherapeutic agent may include one or more of an alkylating agent, anti-metabolite, plant extract, plant alkaloid, nitrosourea, hormone, nucleoside analog, and a nucleotide analog. The anti-cell proliferative chemotherapeutic agent may include one or more of 5-fluorouracil, cyclophosphamide, azathioprine, cyclosporin A, prednisolone, melphalan, chlorambucil, mechlorethamine, busulphan, methotrexate, 6-mercaptopurine, thioguanine, cytosine arabinoside, AZT, 5-azacytidine (5-AZC), bleomycin, actinomycin D, mithramycin, mitomycin C, carmustine, lomustine, semustine, streptozotocin, hydroxyurea, cisplatin, carboplatin, oxiplatin, mitotane, procarbazine, dacarbazine, taxol (paclitaxel), Nab-paclitaxel, vinblastine, vincristine, doxorubicin, dibromomannitol, irinotecan, topotecan, etoposide, teniposide, or pemetrexed.

The inventors recognize that even better compounds for therapeutic use than ones tested within this study may be possible. However, the isothiocyanatostilbenes can serve as scaffold templates to achieve improved specificity and pharmacologic profiles. Overall, the disclosed data identify isothiocyanatostilbenes as effective inhibitors of c-Met phosphorylation that are tolerable in vivo, based on studies using DIDS.

Materials and Methods:

Ethics statement: Investigation has been conducted in accordance with the ethical standards and according to the Declaration of Helsinki and according to national and international guidelines and has been approved by the authors' institutional review board.

Cell culture: DU145, PC3, H1993 and HCC1806 cells were maintained in RPMI 1640 (Cellgro; Manassas, Va.) supplemented with 10% fetal bovine serum (FBS) (Gemini; West Sacramento, Calif.). MDA-MB-231 cells were maintained in DMEM (Cellgro) supplemented with 10% FBS. All cells were obtained from American Type Culture Collection and grown at 37° C. in 5% $CO_2$.

Materials: The stilbene compounds 4,4'-Diisothiocyanatostilbene-2,2'-disulfonic acid (DIDS), 4-acetamido-4'-isothiocyanatostilbene-2,2'-disulfonic acid (SITS), 4,4'-dinitrostilbene-2,2'-disulfonic acid (DNDS) were purchased from Sigma-Aldrich (St. Louis, Mo.) and 4,4'-Diisothiocyanatodihydrostilbene-2,2'-disulfonic acid (H2DIDS) was purchased from Life Technologies (Grand Island, N.Y.). SU11274 was purchased from EMD Millipore (Billerica, Mass.). Recombinant growth factors include: HGF (EMD Millipore), EGF (Sigma-Aldrich), and IGF (PeproTech; Rocky Hill, N.J.).

Western blot analysis: Cells were grown to ~70% confluency prior to treatment. Cells were serum-starved in serum-free media for 30 minutes prior to treatment in complete media or serum-free media for the indicated times. Cell lysates were collected in Laemmli (125 mM Tris, 4% SDS, 0.01% bromophenol blue, 30% sucrose) containing 0.5% β-mercaptoethanol and boiled ~8 minutes. Primary antibodies include: phospho-c-Met (Y1234/1235), phospho-Akt (S473), pEGFR (S845), pIGF-IRβ (Y1135/1136) (Cell Signaling Technology; Beverly, Mass.); α-actin (Sigma-Aldrich), c-Met (C-28) (Life Technologies). Secondary antibodies include: horseradish peroxidase-conjugated anti-rabbit and anti-mouse (GE Healthcare; Pittsburgh, Pa.). ECL 2 was used for chemiluminescent detection (Thermo Scientific; Rockford, Ill.). Densitometry was calculated using ImageJ (NIH).

Wound healing and invasion: DU145 cells were grown to ~100% confluency prior to wounding with the IncuCyte™ WoundMaker™ (Essen Bioscience; Ann Arbor, Mich.) and washed once with complete media. For invasion, cells were covered with Matrigel diluted 1:5 in serum-free RPMI following wounding. Cells were treated with 4 μM DIDS or 25 μM H2DIDS with or without 33 ng/ml HGF or 100 ng/ml EGF for up to 4 days. Images were taken every 4 hours with the IncuCyte™ ZOOM imaging system (Essen Bioscience). Quadruplicate replicates were used in each experiment. Data are presented as percent wound density ±standard error of the mean (S.E.M.).

Scattering assay: DU145 cells were grown to ~50% confluency. Cells were treated overnight with 4 μM DIDS or 25 μM H2DIDS in the presence or absence of 33 ng/ml HGF or 100 ng/ml EGF. Cells were fixed with 4% paraformaldehyde and stained with Oregon Green 488 phalloidin (Invitrogen; Carlsbad, Calif.). Images were acquired on an Eclipse TE300 inverted microscope (Nikon; Tokyo, Japan) with NIS Elements version 4.13.04 software. Presented images were taken using a 10× objective.

Phosphorylation inhibition assay: Z'-LYTE™ Kinase Assay-Tyr6 Peptide kit (Invitrogen) was used to assess the ability of tested compounds to inhibit c-Met phosphorylation. Briefly, 20 μl/well reactions were set up in 96-well plates containing kinase buffer, 200 μM ATP, 4 μM Z-LYTE™ Tyr6 Peptide substrate, 2500 ng/ml c-Met kinase and DIDS or H2DIDS at various concentrations. After 1 hour incubation at room temperature, 10 μl development solution containing site-specific protease was added to each well. Incubation was continued for 1 hour. The reaction was then stopped, and the fluorescent signal ratio of 445 nm (coumarin)/520 nm (fluorescein) was determined on a plate reader (BioTek FLx800™), which reflects the peptide substrate cleavage status and/or the kinase inhibitory activity in the reaction. Appropriate controls were conducted to ensure that DIDS and H2DIDS did not interfere with the reaction or emit detectable fluorescence. The $IC_{50}$ value for each compound was calculated by nonlinear regression of log concentration versus % c-Met phosphorylation ±S.E.M., implemented in GraphPad Prism version 5.0 (GraphPad Software, CA, USA).

2D proliferation: Cells were seeded to ~30% confluency prior to treatment with DIDS or H2DIDS at 0.5 μM, 2 μM, 8 μM, 32 μM, or 64 μM for 24 hours, 48 hours, or 72 hours in complete or serum-free RPMI. A T0 timepoint was also measured. For each timepoint, cells were exposed to Cell Titer Blue reagent (Promega) for 1 hour at 37° C. 5% $CO_2$. Experiments were performed with quadruplicate replicates. Fluorescence was measured using a BioTek Synergy 4 plate reader with Gen5 software.

3D spheroid proliferation: Prior to seeding, cells were incubated with 2.5 ng/μl CellTracker Red (Life Technologies) in complete DMEM lacking Phenol Red for 5 minutes at room temperature then centrifuged at 1000 RPM for 5 minutes. Dyed cells were resuspended in complete DMEM lacking Phenol Red and containing 5% Matrigel before adding 5 μM, 10 μM, 20 μM, or 40 μM DIDS or H2DIDS+/− HGF. The mixture of cells, treatments, and Matrigel in complete media was seeded at 2000 cells/well in a 96 well plate. The plate was centrifuged at 1000 RPM for 3 minutes to collect the cells into the bottom of the plate. Spheroid growth was imaged for up to 80 hours and analyzed for average red object area using the IncuCyte™ ZOOM software. Data are shown as percent change in spheroid growth between T0 and 80 hours with HGF normalized to 100% change in growth. Images were captured by the IncuCyte™ ZOOM imaging system and representative 10× images are shown.

Xenograft studies: All animal experiments were approved by the Institutional Animal Care and Use Committee, University of Louisiana at Monroe, and were handled in strict accordance with good animal practice as defined by the NIH guidelines. Athymic nude mice ($Foxn1^{nu}$/$Foxn1^+$, 4-5 weeks, female) were purchased from Harlan (Indianapolis, Ind.). The mice had free access to standard pellet food and water. The animals were acclimated to animal house facility conditions at a temperature of 18-25° C., with a relative humidity of 55 to 65% and a 12 h light/dark cycle, for one week prior to the experiments. MDA-MB-231/GFP human breast cancer cells were cultured and resuspended in serum-free DMEM medium (20 μl). After anesthesia, cell suspensions ($1 \times 10^6$ cells/20 μl) were inoculated subcutaneously into the second mammary gland fat pad just beneath the nipple of each animal to generate orthotopic breast tumors. At 48 h post-inoculation, the mice were randomly divided into two groups: i) the vehicle-treated control group (n=5), ii) the DIDS-treated group (n=5). Treatment (3×/week) started 5 days post-inoculation with intraperitoneal (i.p.) administered vehicle control (DMSO/saline) or 5 mg/kg DIDS. The dose of DIDS was increased to 10 mg/kg on day 19 post-inoculation. The mice were monitored by measuring tumor volume, body weight, and clinical observation. Tumor volume (V) was calculated by $V=L/2 \times W^2$, where L was the length and W was the width of tumors. The results are presented as average ±S.E.M. Differences among various treatment groups were determined by the analysis of variance (ANOVA) followed by Dunnett's test using PASW statistics version 18. A difference of $P<0.05$ was considered statistically significant as compared to the vehicle-treated control group.

Therapeutic dosages of the isothiocyanatostilbenes, based on the above experiments, are expected to be preferably between 0.5 mg/kg and 50 mg/kg, more preferably between 1 mg/kg and 20 mg/kg, and most preferably between 2.5 mg/kg and 10 mg/kg or a dosage substantially 5 mg/kg.

The isothiocyanatostilbenes could be administered in an variety of routes, including parenteral intra-peritoneal, as was used in animal studies. IM and IV, for example, may also be used due to the good solubility of the disclosed stilbene analogs.

The isothiocyanatostilbenes active agent may be administered in the form of a pharmacologically acceptable salt, solvate, ester, amide, clathrate, stereoisomer, enantiomer, prodrug or analog thereof, or a combination thereof. Salts, solvates, esters, amides, clathrates, stereoisomers, enantiomers, prodrugs, or analogs of the active agents may be prepared using standard procedures known to those skilled in the art of synthetic organic chemistry. For example, basic addition salts are prepared from the neutral drug using conventional means, involving reaction of one or more of the active agent's free hydroxyl groups with a suitable base. Generally, the neutral form of the drug is dissolved in a polar organic solvent such as methanol or ethanol and the base is added thereto. The resulting salt either precipitates or may be brought out of solution by addition of a less polar solvent. Suitable bases for forming basic addition salts include, but are not limited to, inorganic bases such as sodium hydroxide, potassium hydroxide, ammonium hydroxide, calcium hydroxide, trimethylamine, or the like. Preparation of esters involves functionalization of hydroxyl groups which may be present within the molecular structure of the drug. The esters are typically acyl-substituted derivatives of free alcohol groups, i.e., moieties which are derived from carboxylic acids of the formula RCOOH where R is alkyl, and preferably is lower alkyl. Esters can be reconverted to the free acids, if desired, by using conventional hydrogenolysis or hydrolysis procedures. Preparation of amides and prodrugs can be carried out in an analogous manner. Other derivatives and analogs of the active agents may be prepared using standard techniques known to those skilled in the art of synthetic organic chemistry. Unless otherwise stated, the terms analog and derivative may be used interchangeably.

Based on the above experiments and discoveries, other isothiocyanatostilbenes expected to have the cMet inhibiting effect include bioisosteres using the DIDS or H2DIDS as the active scaffold. Bioisosteres for 4,4'-isothiocyanates can be mono or di-substituted 4 and/or 4' nitriles, isocyanates, N-substituted imines, 1,2,4-tetrazoles, and carbamates. Bioisosteres for the 2,2'-disulfonic acid are also be considered including 2 and/or 2'-carboxylates, sulfonamides, phosphonates, tetrazolic acids and thioacids.

Other non-limiting examples of derivatives of cis- and trans active agent derivatives include those in which the hydrogen of one or more of the compounds' hydroxyl groups is replaced to form esters or ethers. Ether formation examples include the addition of alkyl chains such as methyl and ethyl groups, as well as conjugated mono- or disaccharides such as glucose, galactose, maltose, lactose and sucrose. Additional modifications at the hydroxyl groups might include glucuronidation or sulfation. Esterification products include, for example, compounds formed through the addition of amino acid segments such as RGD or KGD or other compounds resulting from the reaction of the isothiocyanatostilbenes hydroxyl groups with carboxylic acids. Additional derivatives include, for example, those compounds that result from the oxidative dimerization of or functional group addition to the parent isothiocyanatostilbenes compound or to a functionalized isothiocyanatostilbenes variant. Examples of these compounds could include materials resulting from the addition of hydroxyl, methoxy and ethoxy groups at the various carbon positions of the active agent. Dimerization results from, for example, the reaction of the ethane bond of one isothiocyanatostilbenes molecule with one of the hydroxyl groups on a second isothiocyanatostilbenes molecule resulting in the formation of a fused ring system. Alkylation at various carbon positions of the active agent could create other derivatives through the addition of groups including methyl, ethyl, and propyl, as well as the addition of larger carbon chains such as 4-methyl-2-pentene, 4-methyl-3-pentene and isopentadiene. Additional derivatives include, for example, compounds that arise from the loss of any of the hydroxyl groups of the isothiocyanatostilbenes parent molecule, addition of hydroxyl groups at alternate positions, and any compound that may arise from the previously mentioned reactions to provide a functionalized variant of the dehydroxylated compound.

Therapeutically acceptable salts of the isothiocyanatostilbenes, and mixtures thereof, fall under the expanse the invention, including disodium or potassium sulfonates, which have better solubility and predicted better activity.

TABLE 1

Properties of DIDS and H2DIDS

| Descriptor | Description | Preferable range | DIDS | H2DIDS |
| --- | --- | --- | --- | --- |
| #Amine | Number of non-conjugated amine groups | 0-1 | 0 | 0 |
| #Amidine | Number of amidine and guanidine groups | 0 | 0 | 0 |
| #Acid | Number of carboxylic acid groups | 0-1 | 2 | 2 |
| #Amide | Number of non-conjugated amide groups | 0-1 | 0 | 0 |
| #Rotor | Number of non-trivial (not CX3), non-hindered (not alkene, amide, small ring) rotatable bonds | 0-15 | 11 | 11 |
| #rtvFG | Number of reactive functional groups; The presence of these groups can lead to false positives in HTS assays and to decomposition, reactivity, or toxicity problems in vivo | 0-2 | 0 | 0 |
| CNS | Predicted central nervous system activity | −2(inactive) +2(active) | −2 | −2 |
| Mol_MW | Molecular weight of the molecule | 130-725 | 454.5 | 456.5 |
| Dipole | Computed dipole moment of the molecule | 1.0-12.5 | 6.67 | 6.997 |
| SASA | Total solvent accessible surface area (SASA) in square angstroms | 300-1000 | 686 | 676 |
| FOSA | Hydrophobic component of the SASA (saturated carbon and attached hydrogen) | 0.0-750 | 2.3 | 32.3 |
| FISA | Hydrophilic component of the SASA (SASA on N, O, H on heteroatoms, carbonyl C) | 7.0-330 | 271 | 251 |
| PISA | P (carbon and attached hydrogen) component of the SASA | 0.0-450 | 227 | 210 |
| WPSA | Weakly polar component of the SASA | 0.0-175 | 184.99 | 182 |
| Volume | Total solvent-accessible volume in cubic angstroms | 500-2000 | 1188 | 1186 |
| DonorHB | Estimated number of hydrogen bonds that would be donated by the solute to water molecules in an aqueous solution. | 0.0-6.0 | 2 | 2 |
| AcceptHB | Estimated number of hydrogen bonds that would be accepted by the solute from water molecules in an aqueous solution. | 2.0-20 | 13 | 13 |
| dip^2/V | Square of the dipole moment divided by the molecular volume. This is the key term in the Kirkwood-Onsager equation for the free energy of solvation of a dipole with volume V | 0.0-0.13 | 0.0374 | 0.0412 |

TABLE 1-continued

Properties of DIDS and H2DIDS

| Descriptor | Description | Preferable range | DIDS | H2DIDS |
|---|---|---|---|---|
| ACxDN^.5/SA | Index of cohesive interaction in solids | 0.0-0.05 | 0.0267 | 0.027 |
| Glob | Globularity descriptor; Globularity is 1.0 for a spherical molecule | 0.75-0.95 | 0.79 | 0.8 |
| QPpolrz | Predicted polarizability in cubic angstroms | 13.0-70.0 | 36.501 | 36.278 |
| QPlogPC16 | Predicted hexadecane/gas partition coefficient | 4.0-18.0 | 14.563 | 14.25 |
| QPlogPoct | Predicted octanol/gas partition coefficient | 8.0-35.0 | 23.629 | 23.509 |
| QPlogPw | Predicted water/gas partition coefficient | 4.0-45 | 18.134 | 17.856 |
| QPlogPo/w | Predicted octanol/water partition coefficient | −2.0-6.5 | 1.431 | 1.549 |
| QPlogS | Predicted aqueous solubility | −6.5-0.5 | −3.3 | −3.151 |
| CIQPlogS | Conformation-independent predicted aqueous solubility | −6.5-0.5 | −3.995 | −4.034 |
| QPlogHERG | Predicted $IC_{50}$ value for blockage of HERG $K^+$ channels | Concern below −5 | −2.389 | −2.136 |
| QPPCaco | Predicted apparent Caco-2 cell permeability in nm/sec. Caco-2 cells are a model for the gut-blood barrier. | <25 poor, >500 great | 1.707 | 2.646 |
| QPlogBB | Predicted brain/blood partition coefficient. Note: QikProp predictions are for orally delivered drugs so, for example, dopamine and serotonin are CNS negative because they are too polar to cross the blood-brain barrier | −3.0-1.2 | −2.536 | −2.258 |
| QPPMDCK | Predicted apparent MDCK cell permeability in nm/sec. MDCK cells are considered to be a good mimic for the blood-brain barrier. | <25 poor, >500 great | 8.415 | 13.17 |
| QPlogKp | Predicted skin permeability | −8.0--1.0 | −4.658 | −4.349 |
| IP(ev) | PM3 calculated ionization potential (negative of HOMO energy) | 7.9-10.5 | 8.828 | 8.871 |
| EA(eV) | PM3 calculated electron affinity (negative of LUMO energy). | −9.0-1.7 | 1.837 | 1.453 |
| #metab | Number of likely metabolic reactions | 1-8 | 0 | 2 |
| QPlogKhsa | Prediction of binding to human serum albumin | −1.5-1.5 | −1.407 | −1.395 |
| HumanOralAbsorption | Predicted qualitative human oral absorption: Predicted qualitative human oral absorption | 1, 2, or 3 for low, medium, or high | 1 | 1 |
| PercentHumanOralAbsorption | Predicted human oral absorption on 0 to 100% scale. | >80% is high <25% is poor | 39.48 | 43.58 |
| SAFluorine | Solvent-accessible surface area of fluorine atoms | 0.0-100 | 0 | 0 |
| SAamideO | Solvent-accessible surface area of amide oxygen atoms | 0.0-35 | 0 | 0 |
| PSA | Van der Waals surface area of polar nitrogen and oxygen atoms and carbonyl carbon atoms | 7.0-200 | 139 | 135 |
| #NandO | Number of nitrogen and oxygen atoms | 2-15 | 8 | 8 |
| RuleOfFive | Number of violations of Lipinski's rule of five | Maximum is 4 | 0 | 0 |
| RuleOfFive | Number of violations of Lipinski's rule of five | Maximum is 4 | 0 | 0 |
| RuleOfThree | Number of violations of Jorgensen's rule of three. The three rules are: QPlogS >−5.7, QP PCaco >22 nm/s, # Primary Metabolites <7. Compounds with fewer (and preferably no) violations of these rules are more likely to be orally available. | Maximum is 3 | 1 | 1 |
| #ringatoms | Number of atoms in a ring | | 12 | 12 |
| #in34 | Number of atoms in 3- or 4-membered rings | | 0 | 0 |

TABLE 1-continued

Properties of DIDS and H2DIDS

| Descriptor | Description | Preferable range | DIDS | H2DIDS |
|---|---|---|---|---|
| #in56 | Number of atoms in 5- or 6-membered rings | | 12 | 12 |
| #noncon | Number of ring atoms not able to form conjugated aromatic systems | | 0 | 0 |
| #nonHatm | Number of heavy atoms (nonhydrogen atoms) | | 28 | 28 |
| Jm | Predicted maximum transdermal transport rate, $K_p$ ` MW ` S (mg $cm^{-2}$ $hr^{-1}$). $K_p$ and S are obtained from the aqueous solubility and skin permeability, QPlogKp and QPlogS. This property is only written to the output file: it is not used in any other calculations. | | 0.004981 | 0.014443 |
| STAR score | Number of property or descriptor values that fall outside the 95% range of similar values for known drugs. A large number of stars suggests that a molecule is less drug-like than molecules with few stars. | 0-5 | 3 | 1 |

Various derivatives of the inventive compounds are described. These derivatives make use of chemically feasible pharmacophores that address potential weaknesses of the original structures noted in the Table 1 above. Additionally, the derivatives below maintain the binding features at c-Met. A base structure (Base Structure 1) is shown below, with variable portions R, $X_1$, $X_2$, $X_3$, Y, and n. Though two Rs are shown, each R may be substituted with, for example, a different element or functional group.

Base Structure 1

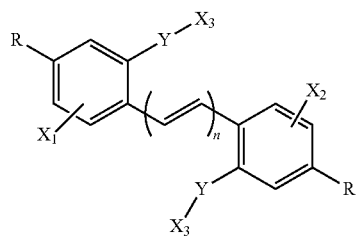

Below are two variations of the base structure above.

Base Structure 2

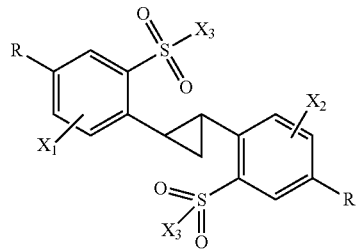

Base Structure 3

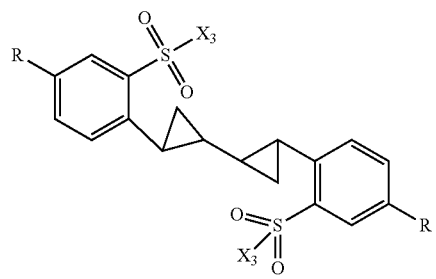

In the above structures, $X_1$ may be the same or different from $X_2$, and either or both may be, for example, H, F, Cl, $CF_3$, and $OCH_3$. n—the number value of carbon bond between the two carbon atoms between the parenthesize—may be one or two, that is a single or double bond respectively. Y may be $SO_2$ or S. The Rs are preferably both N=C=S, but may alternatively be, for example, N=C=O, N=N—$OCH_3$, N=CH—$OCH_3$, $OCH_2OCH_3$, $OCOCCl_3$, and $OCOCF_3$.

In the above structures, the two $X_3$ functional groups may be —OH groups as in DIDS or H2DIDs, or may be represented by the below functional chemicals, where the two $X_3$s may be the same or different functional chemicals:

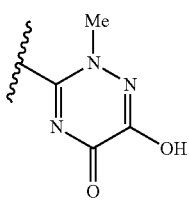

6-hydroxy-2,3-dimethyl-1,2,4-triazin-5(2H)-one

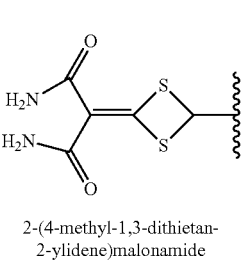

2-(4-methyl-1,3-dithietan-2-ylidene)malonamide

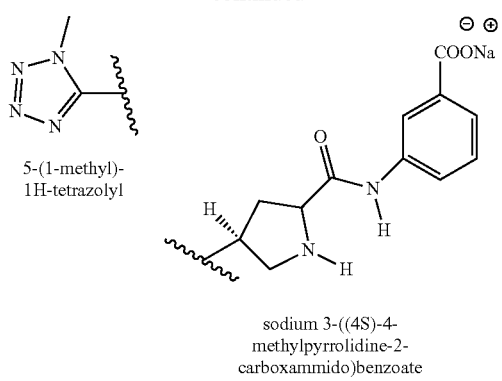
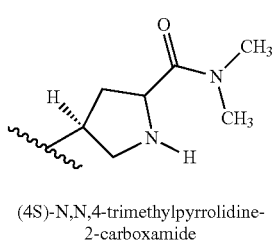
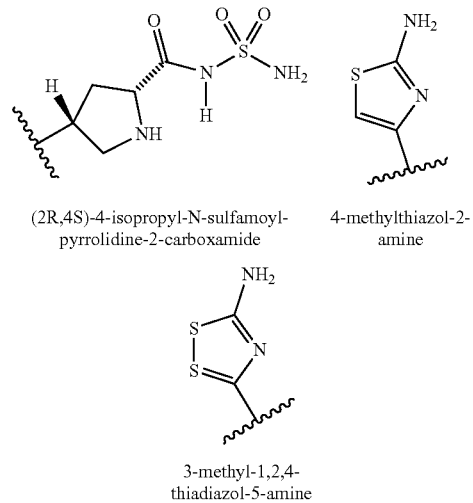
Based on the proposed structural alternatives described above, at least the following group of isothiocyanatostilbenes derivatives are contemplated:
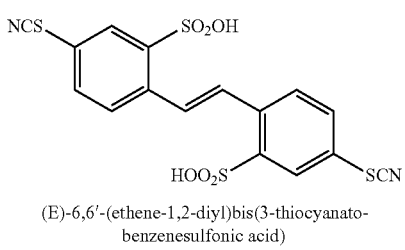
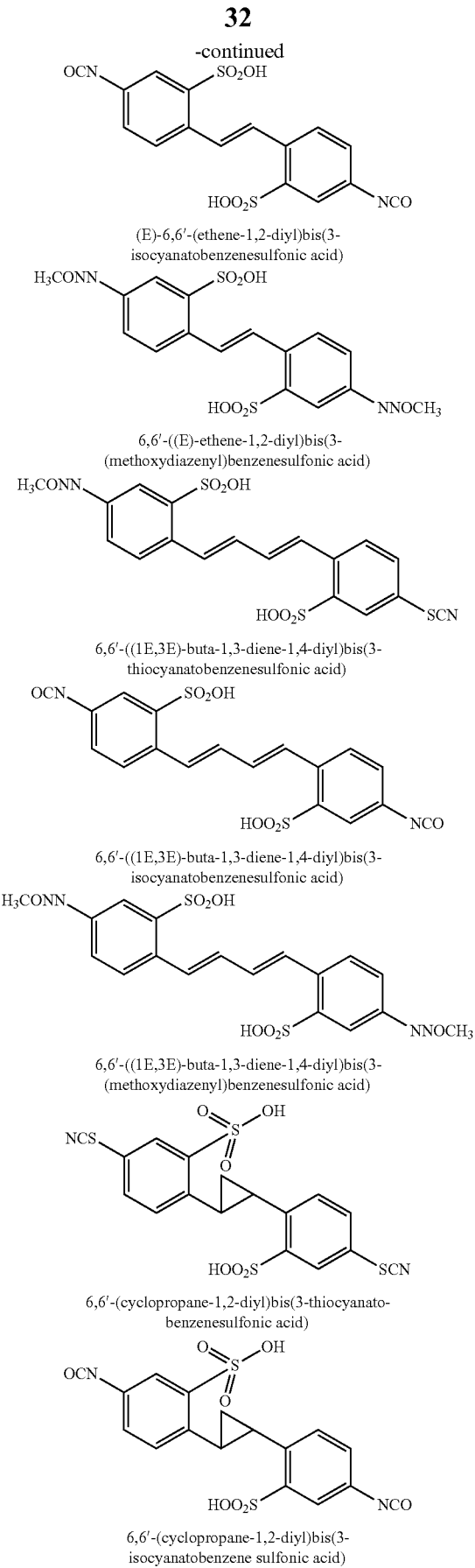

33

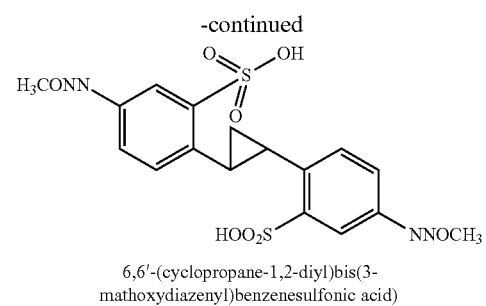

6,6'-(cyclopropane-1,2-diyl)bis(3-mathoxydiazenyl)benzenesulfonic acid)

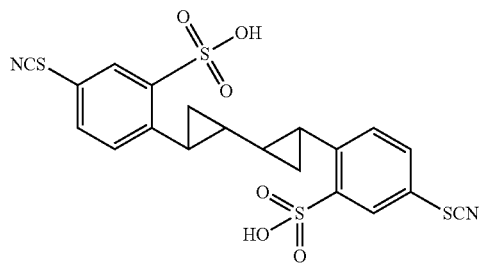

6,6'-(bi(cyclopropane)-2,2'diyl)bis(3-thiocyanatobenzenesulfonic acid)

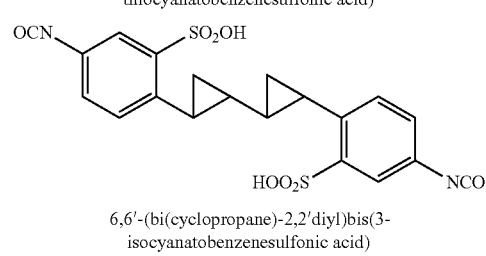

6,6'-(bi(cyclopropane)-2,2'diyl)bis(3-isocyanatobenzenesulfonic acid)

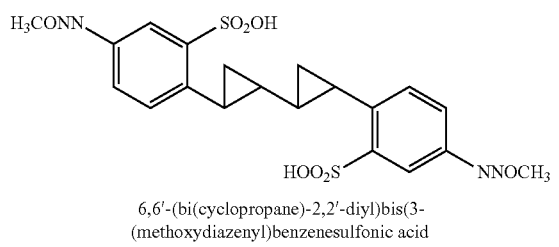

6,6'-(bi(cyclopropane)-2,2'-diyl)bis(3-(methoxydiazenyl)benzenesulfonic acid

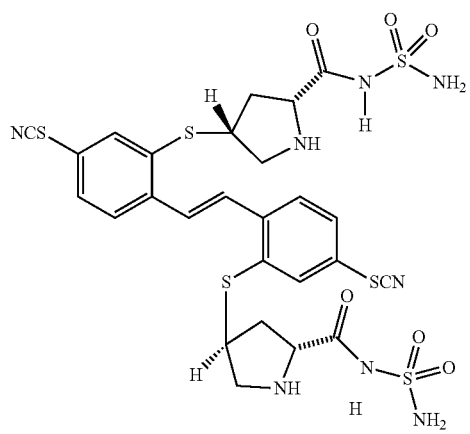

(2R,2'R,4R,4'S)-4,4'-(6,6'-((E)-ethene-1,2-diyl)bis(3-thiocyanato-6,1-phenylene))bis(sulfanediyl)bis(N-sulfamoylpyrrolidine-2-carboxamide)

34

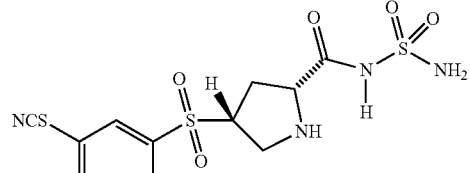

(2R,2'R,4R,4'S)-4,4'-(6,6'-((E)-ethene-1,2-diyl)bis(3-thiocyanato-6,1-phenylene))bis(sulfonediyl)bis(N-sulfamoylpyrrolidine-2-carboxamide)

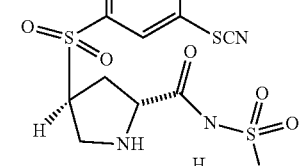

(E)-6,6'-(ethene-1,2-diyl)bis(3-acetaldehydo-benzenesulfonic acid)

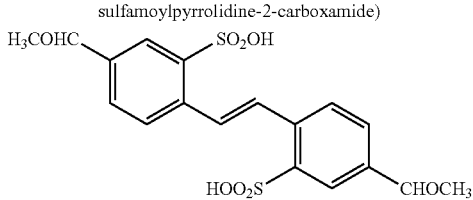

(E)-6,6'-(ethene-1,2-diyl)bis(3-(methoxymethoxy)benzenesulfonic acid

(E)-6,6'-(ethene-1,2-diyl)bis(3-trichloroacetoxy-benzenesulfonic acid)

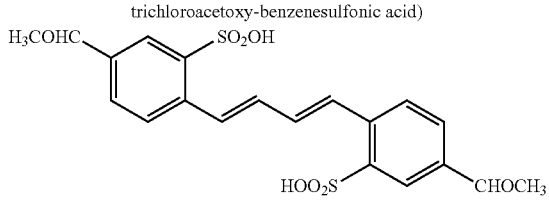

6,6'-((1E,3E)-buta-1,3-diene-1,4-diyl)bis(3-(acetaldehydo)-benzenesulfonic acid)

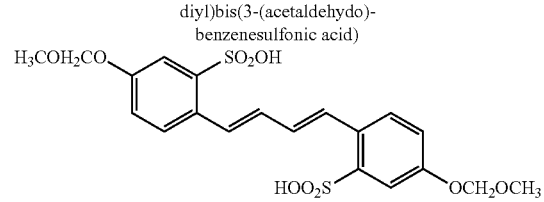

6,6'-((1E,3E)-buta-1,3-diene-1,4-diyl)bis(3-(methoxymethoxy)-benzenesulfonic acid)

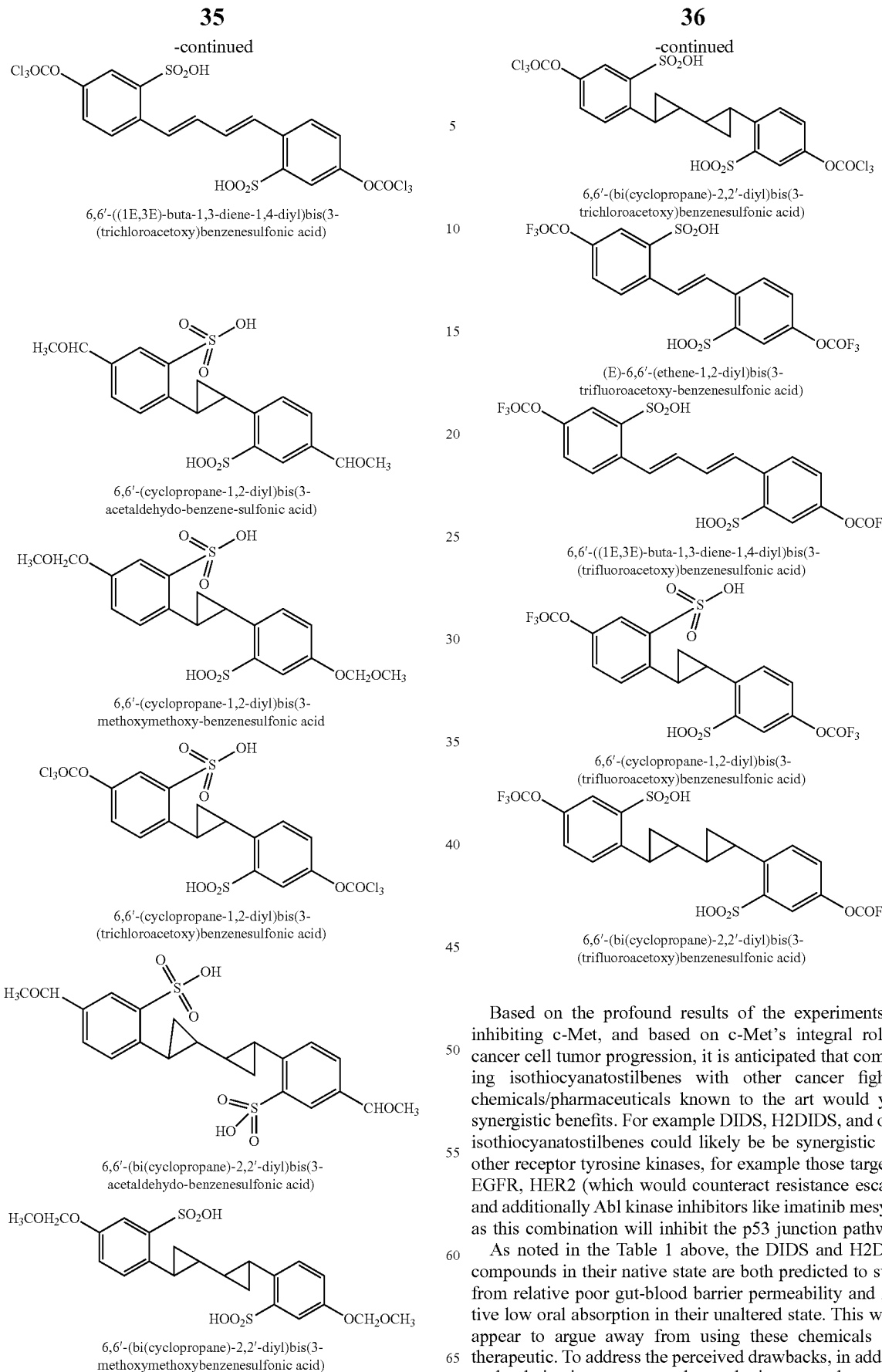

Based on the profound results of the experiments for inhibiting c-Met, and based on c-Met's integral role in cancer cell tumor progression, it is anticipated that combining isothiocyanatostilbenes with other cancer fighting chemicals/pharmaceuticals known to the art would yield synergistic benefits. For example DIDS, H2DIDS, and other isothiocyanatostilbenes could likely be be synergistic with other receptor tyrosine kinases, for example those targeting EGFR, HER2 (which would counteract resistance escape), and additionally Abl kinase inhibitors like imatinib mesylate as this combination will inhibit the p53 junction pathway.

As noted in the Table 1 above, the DIDS and H2DIDS compounds in their native state are both predicted to suffer from relative poor gut-blood barrier permeability and relative low oral absorption in their unaltered state. This would appear to argue away from using these chemicals as a therapeutic. To address the perceived drawbacks, in addition to the derivative structures above, the inventors determined additional methods to increase bioavailability.

Based on the lower relative absorption levels of DIDS and H2DIDS, for example, additional formulations may be used to increase absorption and bioavailability. These additional formulations to increase bioavailability of the active agents include making a cyclodextrin conjugation with the active agents, including, for example, an α-cyclodextrin (α-CD) conjugation, a β-cyclodextrin (β-CD) conjugation, or a γ-cyclodextrin (γ-CD) conjugation (see CD structures below).

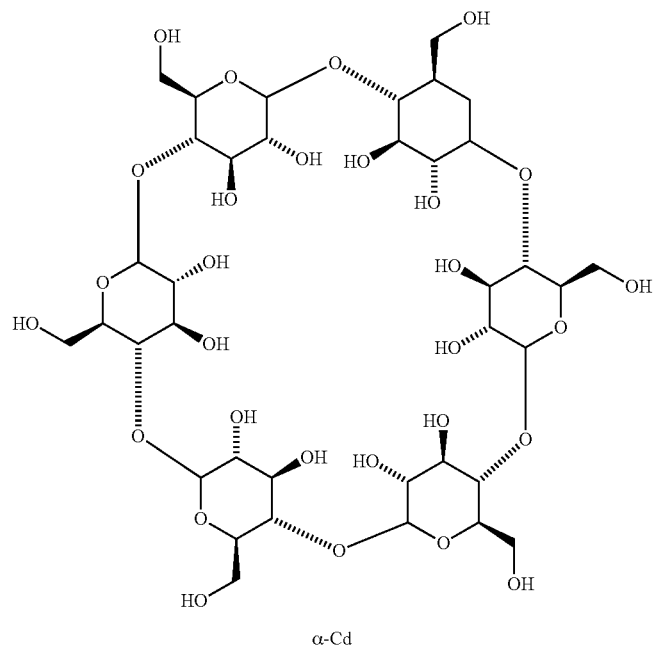

α-Cd

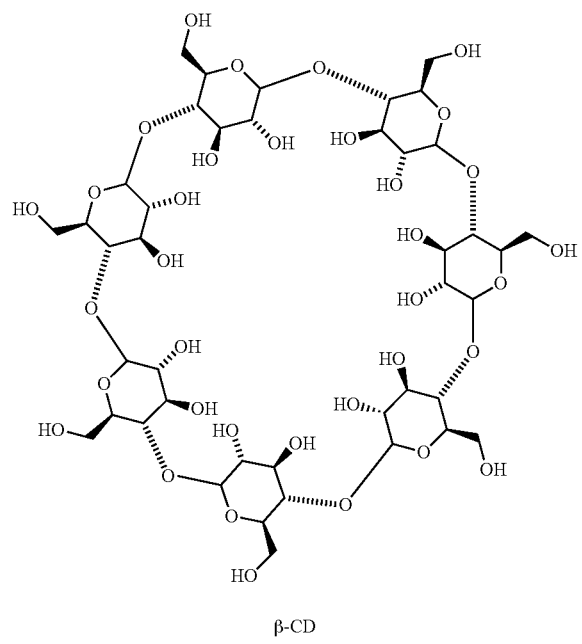

β-CD

-continued

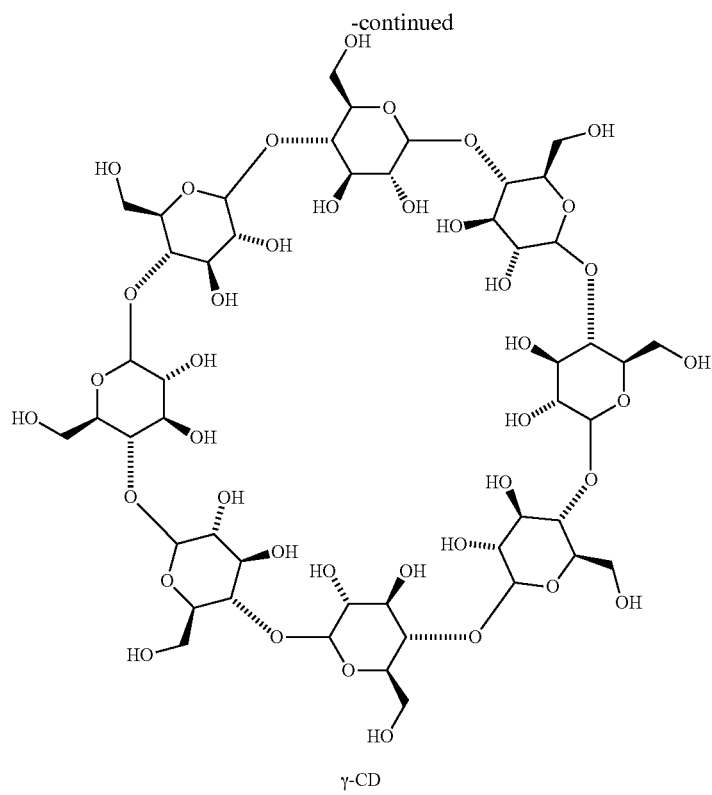

γ-CD

Further additional formulations included preparing the active ingredients as nanoparticles using solution-enhanced dispersion by supercritical carbon dioxide ($CO_2$) (SEDS). Solution-enhanced dispersion by supercritical carbon dioxide ($scCO_2$) is a modified supercritical antisolvent process. In SEDS, for example, a solution containing the solute and $scCO_2$ are atomized via a specially designed coaxial nozzle to obtain droplets of small size and enhance mixing to increase mass transfer rates. In addition to acting as an antisolvent, $scCO_2$ is used as a "dispersing agent" to improve mass transfer between $scCO_2$ and droplets. Therefore, very small particles of active agent can be produced, with increase the surface area to volume ratio of particles the active agent, which increase absorption and bioavailability.

The invention illustratively disclosed herein suitably may explicitly be practiced in the absence of any element which is not specifically disclosed herein. While various embodiments of the present invention have been described in detail, it is apparent that various modifications and alterations of those embodiments will occur to and be readily apparent those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items while only the terms "consisting of" and "consisting only of" are to be construed in the limitative sense.

We claim:

1. A method for treating cancer in a human patient comprising:
    administering to the patient therapeutically effective amount of a first pharmaceutically active agent, wherein the first pharmaceutically active agent is one of an isothiocyanatostilbene and a pharmacologically acceptable salt, solvate, ester, amide, stereoisomer, enantiomer, or prodrug thereof, or a combination thereof;
    wherein the cancer is one of kidney, liver, stomach, breast, brain, lung, ovary, colon, gastric, thyroid, pancreas, head and neck, prostate, liver;
    the isothiocyanatostilbene is selected from a group consisting of 4,4-Diisothiocyanatostilbene-2,2-disulfonic acid (DIDS), 4,4-Diisothiocyanatodihydrostilbene-2,2-disulfonic acid (H2DIDS), 4-acetamido-4'-isothiocyanatostilbene-2,2-disulfonic acid (SITS), and 4,4-dinitrostilbene-2,2'-disulfonic acid (DNDS), and
    the first pharmaceutically active agent is formed as nanoparticles, which nanoparticles are formed using solution-enhanced dispersion by supercritical carbon dioxide.

2. The method of claim 1, wherein the cancer is a solid tumor.

3. The method of claim 1, further comprising the step of administering to the patient a therapeutically effective amount of a first further pharmaceutically active agent.

4. The method of claim 3, wherein the first further pharmaceutically active agent is a c-Met inhibitor.

5. The method of claim 4, wherein c-Met inhibitor is one of Crizotinib (PF-02341066), Cabozantinib (XL184, BMS-907351), Foretinib (GSK1363089), PHA-665752, SU11274, SGX-523, BMS-777607, Tivantinib (ARQ 197), JNJ-38877605, PF-04217903, MGCD-265, Capmatinib (INCB28060), BMS-754807, BMS-794833, AMG-208, MK-2461, Golvatinib (E7050), AMG-458, Tepotinib (EMD 1214063), NVP-BVU972, and NPS-1034, and a pharmacologically acceptable salt, solvate, ester, amide, stereoisomer, enantiomer, or prodrug thereof, or a combination thereof.

6. The method of claim 3, wherein the first further pharmaceutically active agent is one or more of (1) additional isothiocyanatostilbene distinct from the first pharmaceutically active agent, (2) a receptor tyrosine kinase inhibitor (RTKi), (3) an agent that targets non-receptor tyrosine kinases, (4) an anti-cell proliferative chemotherapeutic agent, or of a pharmacologically acceptable salt, solvate, ester, amide, stereoisomer, enantiomer, or prodrug thereof.

7. The method of claim 5, further comprising the step of administering to the patient a second pharmaceutically active agent, where the second pharmaceutically active agent is a further one of an isothiocyanatostilbene and a pharmacologically acceptable salt, solvate, ester, amide, stereoisomer, enantiomer, or prodrug thereof, or a combination thereof, and the first pharmaceutically active agent is distinct from the second pharmaceutically active agent.

8. The method of claim 1, wherein the first pharmaceutically active agent is a isothiocyanatostilbene that has been chemically modified to increase one of bioavailability.

9. The method of claim 1 wherein the first pharmaceutically active agent is in a cyclodextrin conjugation.

10. The method of claim 9, wherein the cyclodextrin conjugation is one of an α-cyclodextrin (α-CD) conjugation, a β-cyclodextrin (β-CD) conjugation, and a γ-cyclodextrin (γ-CD) conjugation.

11. A method for treating cancer in a human patient comprising:
administering to the patient therapeutically effective amount of a first pharmaceutically active agent, wherein the first pharmaceutically active agent is one of an isothiocyanatostilbene and a pharmacologically acceptable salt, solvate, ester, amide, stereoisomer, enantiomer, or prodrug thereof, or a combination thereof;
the cancer is one of kidney, liver, stomach, breast, brain, lung, ovary, colon, gastric, thyroid, pancreas, head and neck, prostate, liver;
and
the isothiocyanatostilbene corresponds to the following formula,

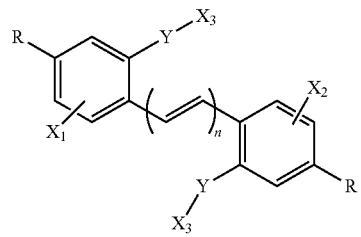

where $X_1$ is one H, F, Cl, $CF_3$, and $OCH_3$;
$X_2$ is one H, F, Cl, $CF_3$, and $OCH_3$;
n is a number value of carbon bond between two carbon atoms between parenthesize, and the number value is one of one, indicating a single bond, and two indicating a double bond;
Y is one of $SO_2$ or S;
each respective R is one of N=C=S, N=C=O, N=N—$OCH_3$, N=CH—$OCH_3$, $OCH_2OCH_3$, $OCOCCl_3$, and $OCOCF_3$, where the respective Rs may be distinct, and;

each respective $X_3$ is one of OH or corresponds to one of the following formulas, where the respective $X_1$s may be distinct, a) 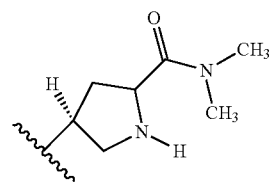

b) 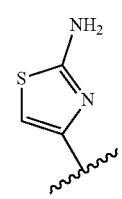

c) 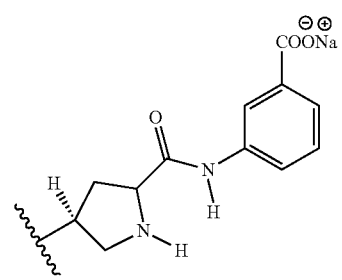

d) 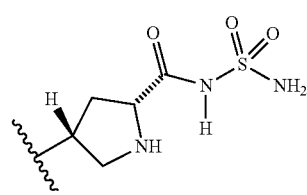

e) 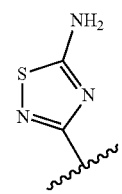

f) 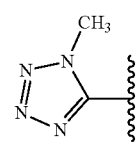

g) 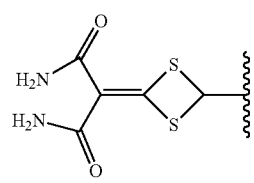

h)

-continued

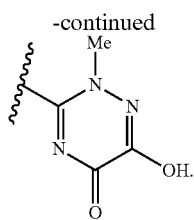

12. A method for treating cancer in a human patient comprising:
    administering to the patient therapeutically effective amount of a first pharmaceutically active agent;
    wherein the first pharmaceutically active agent is one of wherein the isothiocyanatostilbene is selected from a group consisting of 4,4-Diisothiocyanatostilbene-2,2-disulfonic acid (DIDS), 4,4-Diisothiocyanatodihydrostilbene-2,2-disulfonic acid (H2DIDS), 4-acetamido-4'-isothiocyanatostilbene-2,2-disulfonic acid (SITS), and 4,4-dinitrostilbene-2,2'-disulfonic acid (DNDS), and a pharmacologically acceptable salt, solvate, ester, amide, stereoisomer, enantiomer, or prodrug thereof, or a combination thereof; and
    wherein the cancer is one of kidney, liver, stomach, breast, brain, lung, ovary, colon, gastric, thyroid, pancreas, head and neck, prostate, liver.

13. The method of claim 12, wherein the isothiocyanatostilbene is selected from a group consisting of 4,4-Diisothiocyanatostilbene-2,2-disulfonic acid (DIDS), and a pharmacologically acceptable salt, solvate, ester, amide, stereoisomer, enantiomer, or prodrug thereof, or a combination thereof.

14. The method of claim 12, wherein the isothiocyanatostilbene is selected from a group consisting of 4,4-Diisothiocyanatodihydrostilbene-2,2-disulfonic acid (H2DIDS), and a pharmacologically acceptable salt, solvate, ester, amide, stereoisomer, enantiomer, or prodrug thereof, or a combination thereof.

15. The method of claim 12, wherein the isothiocyanatostilbene is selected from a group consisting of 4-acetamido-4'-isothiocyanatostilbene-2,2-disulfonic acid (SITS), and a pharmacologically acceptable salt, solvate, ester, amide, stereoisomer, enantiomer, or prodrug thereof, or a combination thereof.

16. The method of claim 12, wherein the isothiocyanatostilbene is selected from a group consisting of 4,4-dinitrostilbene-2,2'-disulfonic acid (DNDS), and a pharmacologically acceptable salt, solvate, ester, amide, stereoisomer, enantiomer, or prodrug thereof, or a combination thereof.

17. The method of claim 12, wherein the cancer is one of breast, prostate, and lung cancer.

18. The method of claim 12, wherein pharmaceutically active agent is in a drug formulation that provides for gradual release of the pharmaceutically active agent over a period of time 12 hours after administration, and results in substantially constant blood levels in the period of time, with a peak plasma concentration range of the pharmaceutically active agent that is between one of 0.05-10 µM, 0.1-10 µM, 0.1-5.0 µM, and 0.1-1 µM.

19. The method of claim 12, wherein the cancer is a solid tumor.

* * * * *